(12) United States Patent
Li et al.

(10) Patent No.: US 11,126,668 B2
(45) Date of Patent: Sep. 21, 2021

(54) SEARCH SYSTEM, APPARATUS, AND METHOD

(71) Applicant: PATSNAP LIMITED, Grand Cayman (KY)

(72) Inventors: Zhifeng Li, Jiangsu (CN); Markus Haense, Jiangsu (CN); Ali Hussein, London (GB); Yan Zhang, Jiangsu (CN); Xiao Wang, Jiangsu (CN); Ze Ren, Jiangsu (CN)

(73) Assignee: PATSNAP LIMITED, Grand Cayman (KY)

( * ) Notice: Subject to any disclaimer, the term of this patent is extended or adjusted under 35 U.S.C. 154(b) by 202 days.

(21) Appl. No.: 16/432,491

(22) Filed: Jun. 5, 2019

(65) Prior Publication Data
US 2019/0286669 A1 Sep. 19, 2019

Related U.S. Application Data

(63) Continuation of application No. PCT/CN2017/114656, filed on Dec. 5, 2017.
(Continued)

(51) Int. Cl.
*G06F 16/93* (2019.01)
*G06F 16/903* (2019.01)
(Continued)

(52) U.S. Cl.
CPC .............. *G06F 16/93* (2019.01); *G06F 16/34* (2019.01); *G06F 16/90335* (2019.01);
(Continued)

(58) Field of Classification Search
CPC .... G06F 16/93; G06F 16/90335; G06F 16/34; G16C 20/20; G16C 20/80; G16C 20/40; G16C 20/70
(Continued)

(56) References Cited

U.S. PATENT DOCUMENTS

| 10,013,467 B1* | 7/2018 | Brogle | G16C 20/80 |
| 2005/0065733 A1* | 3/2005 | Caron | G16H 70/40 |
| | | | 702/19 |

(Continued)

FOREIGN PATENT DOCUMENTS

| CN | 102929907 A | 2/2013 |
| CN | 105069155 A | 11/2015 |

(Continued)

OTHER PUBLICATIONS

Rhodes et al., "Mining Patents Using Molecular Similarity Search"; https://doi.org/10.1142/9789812772435_0029Cit, Biocomputing 2007, pp. 304-315 (2006) (Year: 2006).*

(Continued)

*Primary Examiner* — Evan Aspinwall
(74) *Attorney, Agent, or Firm* — Meunier Carlin & Curfman LLC

(57) ABSTRACT

Embodiments of the present disclosure relate to systems, methods, and apparatuses for using public information available from a variety of databases and Internet-based resources to obtain and group information to determine related chemical structures, undertake three-dimensional landscape analyses to access those related chemical structures and obtain other information about them including but not limited to patent data, patent family structures, litigation-related information, regulatory and marketing approval information, and other types of information that helps a user understand the medical, technical, and legal landscape associated with certain chemical structures of interest as well as related chemical structures. In addition, the embodiments provide a novel navigation paradigm of search results and content items so that the user can more intuitively and more efficiently get and manipulate information relating to chemi- (Continued)

cal structures that are grouped based on their chemical similarities.

17 Claims, 28 Drawing Sheets

Related U.S. Application Data

(60) Provisional application No. 62/430,289, filed on Dec. 5, 2016.

(51) Int. Cl.
  *G06F 16/34* (2019.01)
  *G16C 20/20* (2019.01)
  *G16C 20/80* (2019.01)
  *G16C 20/40* (2019.01)
  *G16C 20/70* (2019.01)

(52) U.S. Cl.
  CPC .............. *G16C 20/20* (2019.02); *G16C 20/40* (2019.02); *G16C 20/70* (2019.02); *G16C 20/80* (2019.02)

(58) Field of Classification Search
  USPC .......................................................... 707/770
  See application file for complete search history.

(56) References Cited

U.S. PATENT DOCUMENTS

| | | | |
|---|---|---|---|
| 2007/0143322 A1* | 6/2007 | Kothari | G06F 40/194 |
| 2007/0260583 A1* | 11/2007 | Domine | G16C 20/40 |
| 2008/0033999 A1* | 2/2008 | Gardner | G16B 45/00 |
| 2013/0218878 A1 | 8/2013 | Smith et al. | |
| 2014/0372448 A1 | 12/2014 | Olson et al. | |
| 2015/0278349 A1* | 10/2015 | Speier | G06F 16/93 |
| | | | 707/722 |

FOREIGN PATENT DOCUMENTS

| | | |
|---|---|---|
| JP | 2007122431 A | 5/2007 |
| JP | 2007153767 A | 6/2007 |

OTHER PUBLICATIONS

Extended European Search Report issued for European Application No. 17879035.8, dated May 28, 2020.

Bolton, Evan E., et al. "PubChem3D: a new resource for scientists." Journal of cheminformatics 3.1 (2011): 32.

* cited by examiner

(19) United States
(12) Reissued Patent
Rosenblum et al.

(10) Patent Number: US RE42,461 E
(45) Date of Reissued Patent: Jun. 14, 2011

(54) HYDROXY-SUBSTITUTED AZETIDINONE COMPOUNDS USEFUL AS HYPOCHOLESTEROLEMIC AGENTS

(75) Inventors: Stuart B. Rosenblum, West Orange, NJ (US); Sundeep Dugar, San Jose, CA (US); Duane A. Burnett, Bernardsville, NJ (US); John W. Clader, Milton, VT (US); Brian A. McKittrick, New Vernon, NJ (US)

(73) Assignee: Schering Corporation, Kenilworth, NJ (US)

(21) Appl. No.: 12/797,341

(22) PCT Filed: Sep. 14, 1994

(86) PCT No.: PCT/US94/10099
§ 371 (c)(1),
(2), (4) Date: Mar. 18, 1996

(87) PCT Pub. No.: WO95/08532
PCT Pub. Date: Mar. 30, 1995

Related U.S. Patent Documents
Reissue of:
(64) Patent No.: Re. 37,721
Issued: May 28, 2002
Appl. No.: 09/594,996
Filed: Jun. 15, 2000
Which is a Reissue of:
(64) Patent No.: 5,767,115
Issued: Jun. 16, 1998
Appl. No.: 08/617,751
Filed: Mar. 18, 1996

(51) Int. Cl.
*C07D 205/08* (2006.01)
*A61P 9/10* (2006.01)

| | | | |
|---|---|---|---|
| 4,794,108 A | 12/1988 | Kishimoto et al. |
| 4,803,266 A | 2/1989 | Kawashima et al. |
| 4,806,564 A | 2/1989 | Chabala et al. |
| 4,816,477 A | 3/1989 | Girotra et al. |
| 4,834,846 A | 5/1989 | Abramson et al. |
| 4,847,271 A | 7/1989 | Chabala et al. |
| 4,876,365 A | 10/1989 | Kirkup et al. |
| 4,983,597 A | 1/1991 | Yang et al. |

(Continued)

FOREIGN PATENT DOCUMENTS
CA 1063108 9/1979
(Continued)

OTHER PUBLICATIONS

Allain et al., Enzymatic Determination of Total Serum Cholesterol, Clinical Chemical 20:470-475 (1974).

(Continued)

*Primary Examiner* — Mark L Berch
(74) *Attorney, Agent, or Firm* — Ropes & Gray LLP; James F. Haley, Jr.; Carl A. Morales

(57) ABSTRACT

Hydroxy-substituted azetidinone hypocholesterolemic agents of the formula

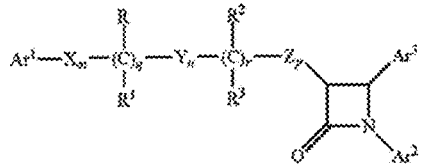

or a pharmaceutically acceptable salt thereof, wherein:
$Ar^1$ and $Ar^2$ are aryl or $R^4$-substituted aryl;
$Ar^3$ is aryl or $R^5$-substituted aryl;
X, Y and Z are —$CH_2$—, —CH(lower alkyl)— or —C(dilower alkyl)—;
R and $R^2$ are —$OR^6$, —$O(CO)R^6$, —$O(CO)OR^9$ or —O(CO)

Fig. 2

UNITED STATES DISTRICT COURT
FOR THE DISTRICT OF NEW JERSEY

SCHERING CORPORATION and
MSP SINGAPORE COMPANY LLC,

*Plaintiffs/Counterclaim Defendants,* v.

MYLAN PHARMACEUTICALS INC.

*Defendant/Counterclaim Plaintiff.*

Civil Action No. 09-6383 (JLL)(MF)

Civil Action No. 10-3085 (JLL)(MF)

SCHERING CORPORATION and
MSP SINGAPORE COMPANY LLC,

*Plaintiffs,* v.

TEVA PHARMACEUTICALS USA, INC.,

*Defendant.*

Civil Action No. 10-1058 (JLL)(MF)

Civil Action No. 10-4473 (JLL)(MF)

(CONSOLIDATED)

FIRST AMENDED COMPLAINT

Plaintiffs Schering Corporation and MSP Singapore Company, LLC (collectively, "Plaintiffs"), by their attorneys, hereby amend their Complaint in *Schering Corporation and MSP Singapore Company LLC v. Mylan Pharmaceuticals Inc.*, Civ. A. No. 10-3085 (JLL)(MF) (D.I. 1), and allege as follows:

NATURE OF THE ACTION

1. This is an action for patent infringement under the patent laws of the United States, Title 35, United States Code, that arises out of the filing by Defendant Mylan Pharmaceuticals Inc. of Abbreviated New Drug Application ("ANDA") No. 201-790 with the U.S. Food and Drug Administration ("FDA") seeking approval to manufacture and sell a generic version of Zetia® prior to the expiration of U.S. Patent No. RE42,461 (the "'461 Patent") and U.S. Patent No. 5,846,966 (the "'966 Patent"). The '461 Patent recently issued on June 14, 2011 and is a reissue of U.S. Patent No. RE 37,721 (the "'721 Patent).

Fig. 3

DEPARTMENT OF HEALTH & HUMAN SERVICES

Food and Drug Administration
Silver Spring, MD 20993

ANDA 078560

APPROVAL

Glenmark Pharmaceuticals, Inc., USA
U.S. Agent for: Glenmark Pharmaceuticals Limited
750 Corporate Drive
Mahwah, NJ 07430
Attention: Kalpana Vanam
         Vice President, Head of Regulatory Affairs, North America Dear Sir or Madam:

This is in reference to your abbreviated new drug application (ANDA) dated October 25, 2007, submitted pursuant to section 505(j) of the Federal Food, Drug, and Cosmetic Act (the FD&C Act), for Ezetimibe Tablets, 10 mg.

We have completed the review of this ANDA and have concluded that adequate information has been presented to demonstrate that the drug is safe and effective for use as recommended in the submitted labeling. Accordingly the ANDA is approved, effective on the date of this letter. The Division of Bioequivalence has determined your Ezetimibe Tablets, 10 mg, to be bioequivalent and, therefore, therapeutically equivalent to the reference listed drug (RLD), Zetia (Ezetimibe), Tablets 10 mg, of MSD International GmbH (MSD). Your dissolution testing should be incorporated into the stability and quality control program using the same method proposed in your ANDA.

The RLD upon which you have based your ANDA, MSD's Zetia (Ezetimibe) Tablets, 10 mg, is subject to periods of patent protection. The following patents and expiration dates (with pediatric exclusivity added) are currently listed in the agency's publication titled Approved Drug Products with Therapeutic Equivalence Evaluations (the "Orange Book"):

| U.S. Patent Number | Expiration Date |
|---|---|
| 7,030,106 (the '106 patent) | July 25, 2022 |
| 7,612,058 (the '058 patent) | April 30, 2026 |
| RE37,721 (the '721 patent) | April 25, 2017 |
| RE42,461 (the '461 patent) | April 25, 2017 |

SEARCH SYSTEM, APPARATUS, AND METHOD

CROSS-REFERENCE TO RELATED APPLICATIONS

This is a Continuation Application, filed under 35 U.S.C. 111, of International Patent Application No. PCT/CN2017/114656, entitled "Systems, Apparatuses, and Methods for Searching and Displaying Information Available in Large Databases According to the Similarity of Chemical Structures Discussed in Them," filed Dec. 5, 2017, which claims priority to U.S. Provisional Application No. 62/430,289, entitled "Searching and Displaying Documents in Large Databases According to the Similarity of Chemical Structures Discussed in Them," filed Dec. 5, 2016, contents of which are incorporated herein by reference in their entireties.

TECHNICAL FIELD

Embodiments of the present disclosure relate to a field of search and, for example, to a search system, apparatus and method.

BACKGROUND

Information spaces, such as the Internet, enterprise networks, document repositories, and information storage and retrieval services allow for widespread access to large collections of information. For example, users commonly use Internet search engines to locate and select desired information on the Internet or within public or proprietary databases relating to products, individual patents and their associated data, simple and complex patent family information, regulatory activity associated with products covered by patents such as FDA approvals, extensions, adjustment, and reductions of patent terms, court and agency activities affecting patent rights and the appropriate interpretation of certain patent claim terms, and medical information associated with certain chemicals including active pharmaceutical ingredients (APIs) found in drug products subject to regulatory oversight and approval. A wide variety of users performing searches relating to chemical structures and patents have an interest in understanding a number of factors and pieces of data that relate to those structures and analyzing and ultimately prioritizing many pieces of information that reside in information silos and discrete databases that are most relevant to their search.

While a manual search and comparison of such information can provide some useful information to a user, the current tools do not provide a system, method or apparatus that gives real-time updates and chemical structure groupings to the user involving similar chemical structures and visualization of chemical spaces.

Search engines assist users in locating items in an information space. Such items can include documents, images, videos, and many other kinds of files known in the art. The search engines typically use search algorithms that employ either literal keyword matching techniques or approximate matching of the words or symbols specified in a user's query or search request. Thus, in conventional searches in discrete data sets and databases, a user searching for information must provide keywords that will hopefully match the desired content. In practice, however, this methodology is little more than a guessing game for both content users and content providers and is particularly difficult when the searches relate to chemical structures. A variety of keywords can be used to conceptual ideas, which can make tagging and keyword searching difficult. In addition, a given combination of keywords is unlikely to be the same between systems providing information regarding particular chemical structures. Accordingly, concept matching or semantic matching of chemical structures and information associated with those structures within search engines can be poor and inconsistent. Conventional search and analysis tools can also be ineffective at ascertaining meaning that is inherent in chemical structures. For many systems, content is expressed in natural language with no convention or chemical structure organization governing the meaning or clustering of the content. Thus, search engines are, in general, unable to locate or group the most appropriate or relevant chemical structure content reliably. It is not currently feasible to rely on the current search tools to group or organize chemical structure content based on the similarity of those structures.

While systems and algorithms that group data based on various pre-defined text parameters are known, they are not useful to relate and correlate information relating to two and three dimensional chemical structures and their associated chemical compound names, including the nomenclature developed by the International Union of Pure and Applied Chemistry (IUPAC); the International Chemical Identifier (InChi) system, which reflects a compound's structure and composition; as well as CAS numbers, which each refer to a single compound and do not contain any information about the structure.

Managing and mapping patent related information in general is known and reference is made to U.S. Pat. No. 9,607,058 to Gupta and U.S. Pat. No. 96,975 to Lundberg. Despite some benefits provided by prior art techniques; these tools nevertheless fall short of providing meaningful groupings of chemical structures and other information that is relevant to those chemical structures, including patent information, to provide users actionable insights regarding certain chemical structures of interest.

SUMMARY

In some embodiments, a search method is provided. The method includes: maintaining a system with at least one database of chemical structures and at least one database of public literature, wherein the public literature includes information regarding chemical structures; receiving from a requesting user a request for information on a target chemical structure provided by the requesting user from a user interface; and in response to the request for information on a target chemical structure, providing a set of related chemical structures to the requesting user, based on the chemical similarity of the plurality of related chemical structures provided to the target chemical structure.

In some embodiments, a search apparatus is further provided. The apparatus includes: a processor and a storage device, wherein the storage device stores processor-executable programs, and the programs include: a module configured to ask by a requesting user for literature information relating to a known chemical structure or related chemical structures; a module configured to, in response to user activities, search a collection of databases, wherein the collection of databases comprises at least one database of chemical structures and at least one database of public literature; and a module configured to identify additional literature or chemical structures that are related to or similar to the known chemical structure and associated literature thereof based on a search method.

In some embodiments, a search system is further provided. The system includes: at least one database of chemical structures, at least one database of public literature, and the search apparatus described above.

The new Patsnap software platform, based around chemical structure searching within and across patents and other literature, incorporates a new tool for visualizing chemical space. This chemical landscaping tool, also called 'Chemscape', is an analytic system, method and apparatus, which arranges chemical structures as squares across a 2D plane based on similarities in chemical structure. Chemical structures that are most similar to each other are found closer to one another. The bigger a change in chemical structure, the more distant they are from one another. This calculation is multiplied across thousands of chemical structures to give a graphical representation of how a selection of structures can be gathered into groups.

Clicking on these representative squares reflecting groupings of similar chemical structures will open up a tool displaying the structure, describing its properties, and providing information on and linking to a wide variety of public material (and some material only available on proprietary databases) including scientific literature, patent materials including patent family information, medical and regulatory information, henceforth collectively referred to as 'literature', that mentions any of the chosen structures of interest.

A 3D layer is then added, which involves the arranged squares (representing the chemical structures), being represented as 3D columns within the tool. In one example, the height of the column is representative of the number of individual 'literature' papers that mention the corresponding chemical structure. In another example, the height of the column is representative of the number of data sources involving the corresponding structure. In another example, the height of the column is representative of the proteins or other chemical entities that corresponding structure is grouped with due to the their chemical structure similarities.

This 'Chemscape' tool can, in an optional embodiment, be animated to give a dynamic overview of how 'literature' mentioning the corresponding chemical structures have been published over time. This includes 3D columns that reflect the publication dates of the 'literature' mentioning the structures, and the columns increase in height as a timeline increases in length.

The 2D squares and 3D columns can, in an optional embodiment, be highlighted based on information relating to the underlying chemical structures associated with the data set, such as structural similarity scores in reference to a query structure, regulatory approval information, clinical trial phases, statuses, and sources of the corresponding chemical structure information. These squares and columns can also, in another optional embodiment, be highlighted based on information relating to the patents or literature mentioning the chemical structures, such as patent classification codes, publication dates, patent filing or expiration dates, assignees, normalized assignees, inventors on patents, and scientific references mentioning the chemical structure.

On top of this chemical structure and associated information visualization tool, is the ability to search across literature (including associated patents and scientific references) based on keyword searching within 'literature' text, or information searching across 'literature' metadata. Upon inputting a search query, the 3D columns change, in an optional embodiment, in height based on refinement of the corresponding 'literature' to reflect the number of refined 'literature' results that mention the chemical structure and qualify the results based on the user-inputted query refinement information.

The present system, apparatus and method provide a novel two-dimensional matrix reflecting a grouping of chemical structures based on the similarity of their chemical structures and associated literature that the user can analyze along with the grouped chemical structures to better understand the legal, regulatory, and medical status of them.

Embodiments of the present disclosure relate to systems, methods, and apparatuses for improving a search for chemical structure content in an information space within and across patents and other literature available in a wide range of databases, and it incorporates a new tool for visualizing chemical space in landscape formats. More particularly, embodiments of the present disclosure relate to systems, methods, and apparatuses for using public information available from a variety of databases and Internet-based resources to obtain and group information to determine related chemical structures, undertake three-dimensional landscape analyses to access those related chemical structures and obtain other information about them including but not limited to patent data, patent family structures, litigation-related information, regulatory and marketing approval information, and other types of information that helps a user understand the medical, technical, and legal landscape associated with certain chemical structures of interest as well as related chemical structures.

BRIEF DESCRIPTION OF THE DRAWINGS

The present disclosure will now be described more fully hereinafter with reference to the accompanying drawings, which illustrate various embodiments of the disclosure. This disclosure, however, may be embodied in many different forms and should not be construed as limited to the embodiments set forth herein. Rather, these embodiments are provided so that the present disclosure will be thorough and complete, and will fully convey the scope of the disclosure to those skilled in the art. It is to be fully recognized that the different teachings of the various embodiments discussed below may be employed separately or in any suitable combination to produce desired results. The various characteristics mentioned above, as well as other features and characteristics described in more detail below, will be readily apparent to those skilled in the art upon reading the following detailed description of the various embodiments, and by referring to the accompanying drawings. In the drawings and description that follow, like parts are marked throughout the specification and drawings with the same reference numerals, respectively. The prime notation, if used, indicates similar elements in alternative embodiments. The drawings are not necessarily to scale. Certain features of the present disclosure may be shown exaggerated in scale or in somewhat schematic form and some details of conventional elements may not be shown in the interest of clarity and conciseness.

FIG. 2 is a representative excerpt of a patent application accessible through an exemplary method according to an embodiment of the disclosure.

FIG. 3 is a representative excerpt of a court filing accessible through an exemplary method according to an embodiment of the disclosure.

FIG. 4 is a representative excerpt of Food and Drug Administration (FDA) correspondence accessible through an exemplary method according to an embodiment of the disclosure.

FIG. 5 is a representative excerpt of public information regarding drug exclusivity expiration dates accessible through an exemplary method according to an embodiment of the disclosure.

FIG. 6 is a screenshot of public information reflecting regulatory approval and drug exclusivity information accessible through an exemplary method according to an embodiment of the disclosure.

FIG. 9 is a screenshot excerpt of sample patent and associated patent information accessible through an exemplary method according to an embodiment of the disclosure.

FIG. 10 is a screenshot excerpt of sample legal information associated with a sample patent accessible through an exemplary method according to an embodiment of the disclosure.

DESCRIPTION OF THE EMBODIMENTS

Figure 1:
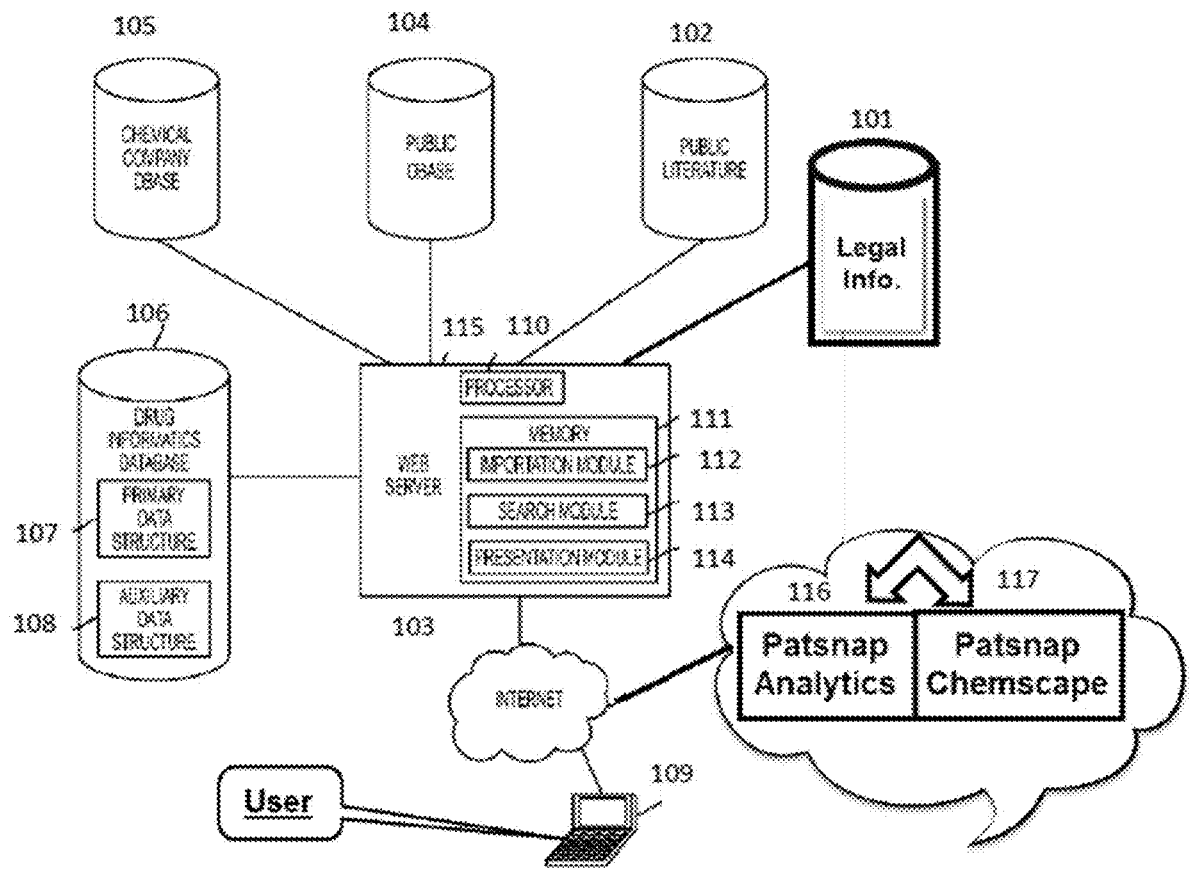
FIG. 1 is a schematic block diagram of an exemplary method according to an embodiment of the disclosure.

Embodiments of the present disclosure are described in the accompanying drawings, wherein like parts are designated by like reference numerals throughout, and wherein the leftmost digit of each reference number refers to the drawing number of the figure in which the referenced part first appears.

The disclosure includes a method for visually mapping chemical structures based on their structural similarities and associating a wide variety of literature relating to said chemical structures comprising maintaining a system with at least one database of chemical structures and at least one database of public literature, wherein said public literature includes information regarding chemical structures; receiving from a requesting user a request for information on a target chemical structure provided by the requesting user from a user interface generated on a display by at least one computer processor; in response to the request for information on a target chemical structure, providing a set of related chemical structures to the requesting user, based on the chemical similarity of the plurality of related chemical structures provided to the target chemical structure; wherein said at least one database of chemical structures is stored on at least one storage device; wherein said at least one database of public literature is stored on at least one storage device.

In general, embodiments of the present disclosure provide a novel approach for more efficient searching, knowledge discovery, content discovery, and browsing or navigating in an information space to review and associate chemical structures and literature information. In some embodiments, systems and methods provide a 2D and 3D oriented structure for organizing and accessing information associated with chemical structures. Optional embodiments of the present disclosure leverage the semantics of literature, shape of the chemical structures, fingerprinting, or Tanimoto scoring and the goal of a user's search to provide a novel two and three dimensional navigation paradigm of search results and content items so the user can more intuitively and more efficiently get access to and analyze information related to chemical structures housed within at least one database of chemical structures.

In some embodiments, a user can navigate or descend through various levels or nodes of literature related to chemical structures. This information can be presented in any type of two dimensional or three-dimensional data structure or graph, as well as hierarchical or non-hierarchical outputs. The information outputs may be structured to provide a progressively narrower scope of subject matter related to a chemical structure, which can help users to search and/or browse for content of a specific type or semantic context and then drill down on certain content of interest using a visual representation of that information.

A content source can be any body of information, including databases having individual items of content. An example of such a content source is the World Wide Web, where content item can be a resource accessible via a uniform resource locator ("URL") on the Internet. Content items may also include URLs that correspond to web pages, images, files, or other items that can be provided to a user, such as via a browser or other type of content interface applications.

In some embodiments, the semantic meaning of content items can be based on interpretations of interactions users take to organize and review the content items within an organized content structure. The semantics of content items may also be determined based on a user's declarations or inputs in the database about the content items.

Some embodiments are based on systems and methods for determining the relationship of content items as indicated by user-derived information. User-derived information may be any information that originates from an individual user, including the user requesting the search, a group of users, or an entire community of users. That is, the embodiments provide mechanisms and techniques for improving and capturing relationships between literature and chemical structures as the information is organized by users in a user community, based on, among other things, user interactions with the information in at least one database. Accordingly, some embodiments provide an organized report of related chemical structures, so that users can search for target chemical structures, navigate or browse chemical structures, organize literature information, and perform other operations on information within that report of chemical structures. Any of those operations can indicate importance of the literature related to chemical structures. User-derived information can be anonymous or identified with one or more users or user groups.

In some embodiments, a user can navigate through a tool that provides organized content structure to discover and view target chemical structures and related chemical structures. The organization and grouping of the chemical structures and related literature information that are provided to users through a two-dimensional or three-dimensional report can provide valuable contextual information that allows the user to take some action with respect to the target chemical structure.

An organized content structure may be implemented in various ways, including providing visual reports that incorporate several different kinds of folders, trees, lists, graphs, databases, and/or other appropriate data structures known in the art. An organized content structure may be delivered locally for access by a single user through a display on a local computer or saved within a platform for simultaneous access by many users. Global implementations can include cloud-based systems known in the art or distributed systems where portions of the organized content structure may exist on a plurality of computing systems. The storage for a local organized content structure may be implemented physically on a user's own client device, such as a hard disk drive, or implemented virtually using remote services over a network, such as cloud-based storage. In addition, a local organized content structure may comprise a similar semantic organization as a global organized content structure, but the local organized content structure may content items that are retained for the specific purposes of a user.

Embodiments of the present disclosure can apply to repositories of literature that are small or moderate in size, as well as the largest distributed repositories of literature, such as databases that retain and index documents obtained from web crawlers, etc. operating on the World Wide Web. Embodiments of the disclosure provide the user with a more controlled and interactive approach to locating literature relating to chemical structures. The embodiments provide various modalities of searching for literature using queries and navigating an organized structure, such as a hierarchy of interactive menus or folders in a user interface, alone or in combination.

Overview of the Chemscape Tool

Embodiments of the disclosure can provide a search engine configured to generate an output of chemical structures that are grouped based on their structural similarities, as well as additional literature that relates in some manner to one or more of those chemical structures, for a particular user for the purpose of providing a variety of information relating to those structures including medical data, regulatory approvals, legal information (including patent information). That is, a user can ask for literature information relating to a known chemical structure or related chemical structures and navigate that information using two and three dimensional visualization tools. In response to user activities, the Chemscape tool may search a collection of databases, and based on a variety of known search techniques further discussed below, the tool may identify additional literature or chemical structures that are related to or similar to the known chemical structure and its associated literature. The determination of chemical structure similarity can be optionally made based on actions that other users have taken within the organized content structure to organize and associate any of the known set of documents with other content items.

Embodiments of the disclosure are directed to systems, methods, and apparatuses for providing similar chemical structures and associated literature in this fashion, using association criteria as discussed in the example above, as well as more complex relational criteria as described below.

The disclosure also includes a method of automatically computing, mapping and accessing chemical structure similarities in conjunction with corresponding non-chemical (patent, legal and medical data) records comprising: (a) Selecting/entering a target chemical structure from a data base using a User Interface generated on a display by a processor of a computer system, where the user interface being associated to a patent-related search engine linked to the data base, the search engine and the data base being hosted in either a first memory of the computer system or in a remotely located second memory; and (b) Obtaining from the data base chemical structure records related to the target chemical structure to create via the processor a 2D-map from a user-input method and from a first data sets of chemical records stored in the first memory or the second memory.

The Chemscape tool is based around chemical structure searching within and across patents and other literature, incorporates a new tool for visualizing chemical space. This chemical landscaping tool is an analytic system, method and apparatus, which arranges chemical structures as squares across a 2D plane based on similarities in their structure. Chemical structures that are most similar to each other are found closer to one another. The bigger a change in chemical structure, the more distant they are from one another. This calculation is multiplied across thousands of structures to give a graphical representation of how a selection of structures can be gathered into groups.

Clicking on these representative squares reflecting groupings of similar chemical structures will open up a tool displaying the structure, describing its properties, and providing information on and linking to a wide variety of public material (and some material only available on proprietary databases) including scientific literature, patent materials including patent family information, medical and regulatory information, henceforth collectively referred to as 'literature', that mentions any of the chosen structures of interest.

A 3D layer is then added, which involves the arranged squares (representing the chemical structures), being represented as 3D columns within the tool. In one example, the height of the column is representative of the number of individual 'literature' papers that mention the corresponding chemical structure. In another example, the height of the column is representative of the number of data sources involving the corresponding structure. In another example, the height of the column is representative of the proteins or other chemical entities that corresponding structure is grouped with due to their chemical structure similarities.

This 'Chemscape' tool can be animated to give a dynamic overview of how 'literature' mentioning the corresponding chemical structures have been published over time. This includes 3D columns that reflect the publication dates of the 'literature' mentioning the structures, and the columns increase in height as a timeline increases in length.

The 2D squares and 3D columns can, in an optional embodiment, be highlighted based on information relating to the underlying chemical structures associated with the data set, such as structural similarity scores in reference to a query structure, regulatory approval information, clinical trial phases, statuses, and sources of the corresponding chemical structure information. These squares and columns can also, in another optional embodiment, be highlighted based on information relating to the patents or literature mentioning the chemical structures, such as patent classification codes, publication dates, patent filing or expiration dates, assignees, normalized assignees, inventors on patents, and scientific references mentioning the chemical structure.

On top of this chemical structure and associated information visualization tool, is the ability to search across literature (including associated patents and scientific references) based on keyword searching within 'literature' text, or information searching across 'literature' metadata. Upon inputting a search query, the 3D columns change, in an optional embodiment, in height based on refinement of the corresponding 'literature' to reflect the number of refined 'literature' results that mention the chemical structure and qualify the results based on the user-inputted query refinement information.

The present system, method, and apparatus provide a novel two-dimensional matrix reflecting a grouping of chemical structures based on the similarity of their chemical structures and associated literature that the user can analyze along with the grouped chemical structures to better understand the legal, regulatory, and medical status of them.

In optional embodiments, the selecting occurs via a menu/ or automation function activated via the processor using a first method to determine a first set of molecular similarities with respect to the target chemical structure, where the method includes at least a Tanimoto Scoring and Fingerprinting, a Semantic similarity, or a Shape similarity among the chemical structures.

In optional embodiments, the generating occurs via the processor to provide a first non-linear clustering map of similar chemical structure records using the selected similarity determination method.

Additionally, the results are displayed optionally on a computer screen and reflect the first non-linear clustering of the chemical structures records on a plane as a 2d-map according to a 1st graphic distribution method of the similar chemical structures.

In other embodiments, the results obtained involve a single or a plurality of user-selected non-chemical secondary data set records from a source/library hosted in the first or second memory and linked to the 2d-map of chemical structure similar records.

The tool may also optionally arrange and display the selectable secondary data set records related to the 2D-map chemical structures as a 3D-map of graphic elements to simultaneously and visually link-associate the non-chemical secondary data set records to the 2D-map of chemical structures. The tool may further display the secondary data set records according to a particular and selectable task without exiting the search engine to access and visualize the secondary data set records. The records may be displayed as 3D cuboidal, cylindrical, or other shaped bar, with height of 3D bar representing the count of secondary data records.

The user may also access the secondary non-chemical data set records linked to the chemical records of the 2D-map via the 3D-map by clicking on one or several select graphic element via an inputting or a pointing device.

Literature Available to Chemscape Tool

Search results provided by embodiments of the present disclosure may operate on the following data objects, databases, or information entities, though these lists are not intended to be limiting as other similar data items may also be included:

1) As mentioned above, content items (sometimes referred to as "content," or "items") are discrete information resources. Content items can be, for example, web pages or other components of web pages that can be specified and stored as a reference (for example, by a Uniform Resource Locator, or "URL"). Content items can also be videos, sound files, images, and documents of all kinds, including PDF files, word processing files (e.g., Microsoft Word), spreadsheets (e.g., Microsoft Excel), presentation files (e.g., Microsoft PowerPoint), graphics files, source code files, executable files, databases, messages, configuration files, data files, and the like. Content items can be accessed, reviewed, modified, and saved by users of systems implemented by any of the embodiments.

2) Databases that include information relating to patent applications, published patents, granted patents, patent families, patent terminal disclaimers, legal decisions and opinions relating to patent validity or infringement, interpretation of patent claim terms, patent term adjustments and extensions, regulatory activities relating to patents (including adjustment of patent terms for delay due to regulatory approval, orphan drugs, and new approved uses) and medical information relating to adverse events, approved uses and treatments, as well as medical and scientific literature databases.

Embodiments of the System

The system of the present disclosure may comprise any device and/or means for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device.

A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, auto-sizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

The present disclosure can be realized in hardware, software, or a combination of hardware and software. The disclosure can be realized in a centralized fashion in one computer system, or in a distributed fashion where different elements are spread across several interconnected computer systems. Any kind of computer system or other apparatus adapted for carrying out the methods described herein is suitable. A typical combination of hardware and software can be a general-purpose computer system with a computer program that, when being loaded and executed, controls the computer system such that it carries out the methods described herein.

Methods of Use

The story of the pharmaceutical drug ZETIA and the need to use the Chemscape tool to a) find similar chemical structure to develop new drugs, b) use data from patents and medical records to assist the researchers in develop new drugs and to avoid litigation demonstrate the novelty and uniqueness of the present disclosure.

Medical related patents represent an important business tool to promote innovation by securing companies a way to protect their investment in new and useful discoveries. Also such companies can have access, via patent licensing negotiations, to other useful developments coming from a third party's patents of interest.

Patents granted for and related to medical drugs face a tougher challenge considering the FDA regulations and also the continuous legal disputes between the so called medical Brand companies (BC) and Generic companies.

As it is well known, once the life of patent developed by a Brand like company approaches expiration, the Generic like companies will be already ready to manufacture and sell an identical medical drug described and claimed in that patent.

As it is well known, once a patent application filed by a Brand like company (BLC) is published, other Brand like companies or Generic like company will try to "design around" the patents, or develop new drugs by finding "similar chemical structures", or try to patent these new drugs and avoid such publications as prior art.

The patent literature and the non patent literature related to medical drugs is very extensive and the amount of new data and literature will only grow in the future.

There is a need for an increased accuracy and speed to determine via a tool like Chemscape similarities between chemical structures in order to develop new medical drugs and identify a variety of risks associated with the pursuit of various chemical structures as potential active pharmaceutical ingredients in future development efforts.

If a new chemical structure is discovered or a known chemical structure needs to be used in new drugs, there is a need for a tool to collect, process and display automatically all the related chemical data, the patent and the medical data in a manner that meet all the research, patent, legal, medical etc. standards and rules.

Unlike in any other field, the development of a new drug needs to follow many regulations and most important, needs to avoid patent litigation.

Although the present disclosure provides certain embodiments and applications, other embodiments that are apparent to those of ordinary skill in the art, including embodiments, which do not provide all of the features and advantages set forth herein, are also within the scope of this disclosure.

The present disclosure, as already noted, can be embedded in a computer program product, such as a computer-readable storage medium or device which when loaded in a computer system is able to carry out the different methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The foregoing disclosure has been set forth merely to illustrate the disclosure and is not intended to be limiting. It will be appreciated that modifications, variations and additional embodiments are covered by the above teachings and within the purview of the appended claims without departing from the spirit and intended scope of the disclosure. Other logic may also be provided as part of the exemplary embodiments but are left out here so as not to obfuscate the present disclosure. Since modifications of the disclosed embodiments incorporating the spirit and substance of the disclosure may occur to persons skilled in the art, the disclosure should be construed to include everything within the scope of the appended claims and equivalents thereof.

The following examples pertain to further embodiments. Specifics in the examples may be used anywhere in one or more embodiments.

Example 1 is a method of automatically computing, mapping and accessing chemical structure similarities in conjunction with corresponding non-chemical (patent, legal and medical data) records comprising: a) Selecting/entering a target chemical structure from a data base using a User Interface generated on a display by a processor of a computer system, where the user interface being associated to a patent-related search engine linked to the data base, the search engine and the data base being hosted in either a first memory of the computer system or in a remotely located second memory; and b) Obtaining from the data base chemical structure records related to the target chemical structure to create via the processor a 2D-map from a user-input method and from a first data sets of chemical records stored in the first memory or the second memory.

Example 2 is a method of automatically computing, mapping and accessing chemical structure similarities in conjunction with corresponding non-chemical data including patent, legal and medical records, the method comprising: a) Selecting/entering a target chemical structure from a data base using a User Interface generated on a display by a processor of a computer system, where the user interface being associated to a patents' related search engine linked to the data base, the search engine and the data base being hosted in either a first memory of the computer system or in a remotely located second memory; b) Obtaining from the data base chemical structure records related to the target chemical structure to create via the processor a 2D-map from a user-input method and from a first data sets of chemical records stored in the first memory or the second memory; c) Selecting via a menu/or automation function activated via the processor a first method to calculate or evaluate a first set of molecular similarities with respect to the target chemical structure, where the method including at least one of a Tanimoto Scoring and Fingerprinting, a Semantic similarity or a Shape similarity; d) Generating via the processor a first non-linear clustering map of similar chemical structure records using the selected similarity method. e) Displaying on a computer screen the first non-linear clustering of the chemical structures records on a plane as 2d-map according to a 1st graphic distribution method of the similar chemical structures. f) Obtaining a single or a plurality of user-selected non-chemical secondary data set records from a source/library hosted in the first or second memory and linked to the 2d-map of chemical structure similar records. g) Arranging and displaying the selectable secondary data set records related to the 2D-map chemical structures as a 3D-map of graphic elements to simultaneously and visually link-associate the non-chemical secondary data set records to the 2D-map of chemical structures. h) Accessing the secondary non-chemical data set records linked to the chemical records of the 2D-map via the 3D-map by clicking on one or several select graphic element via an inputting or a pointing device.

Example 3 includes a method of automatically computing, mapping and accessing chemical structure similarities of example 2, further including the step of displaying the secondary data set records according to a particular and selectable task without exiting the search engine to access and visualize the secondary data set records.

Example 4 includes a method of automatically computing, mapping and accessing chemical structure similarities of example 2, further including repeating step (c) by changing the method to evaluate a molecular similarity/dissimilarity.

Example 5 is a method of automatically computing, mapping and accessing chemical structure similarities where the 3D map is used to open and visualize simultaneously the chemical info and at least partially the non-chemical data including.

In following examples, the search method, apparatus and system based on chemical structures are exemplarily described. FIG. 1 is a schematic block diagram of an exemplary method according to an embodiment of the disclosure. As shown in FIG. 1, a searching system includes a variety of data sources and a web server 103. The data sources may include: legal information 101, public literature 102, a public database 104, a chemical company database 105 and a drug informatics database 106. The drug informatics database 106 may include a primary data structure 107 and an auxiliary data structure 108.

The web server 103 includes a processor 110 and a memory 111. The memory 111 may include an importation module 112, a search module 113 and a presentation module 114. By summarizing the data from the above-mentioned data sources, the system provides users with an Internet-based chemical structure search service under the cooperation of various modules in the web server 103 of the system. The system can work with the Patsnap Analytics system and the Patsnap Chemscape system.

FIG. 2 is a representative excerpt of a patent application accessible through an exemplary method according to an embodiment of the disclosure. A U.S. Pat. No. RE42, 461E is shown in FIG. 2. The search apparatus and system of the embodiments of the present disclosure may extract chemical terms from the patent by utilizing the technique of semantic analysis, and convert the chemical terms into a chemical structure, thereby implementing the search based on the chemical structure. In some embodiments, the chemical structure may also be directly extracted from the patent.

Figures 5, 6:
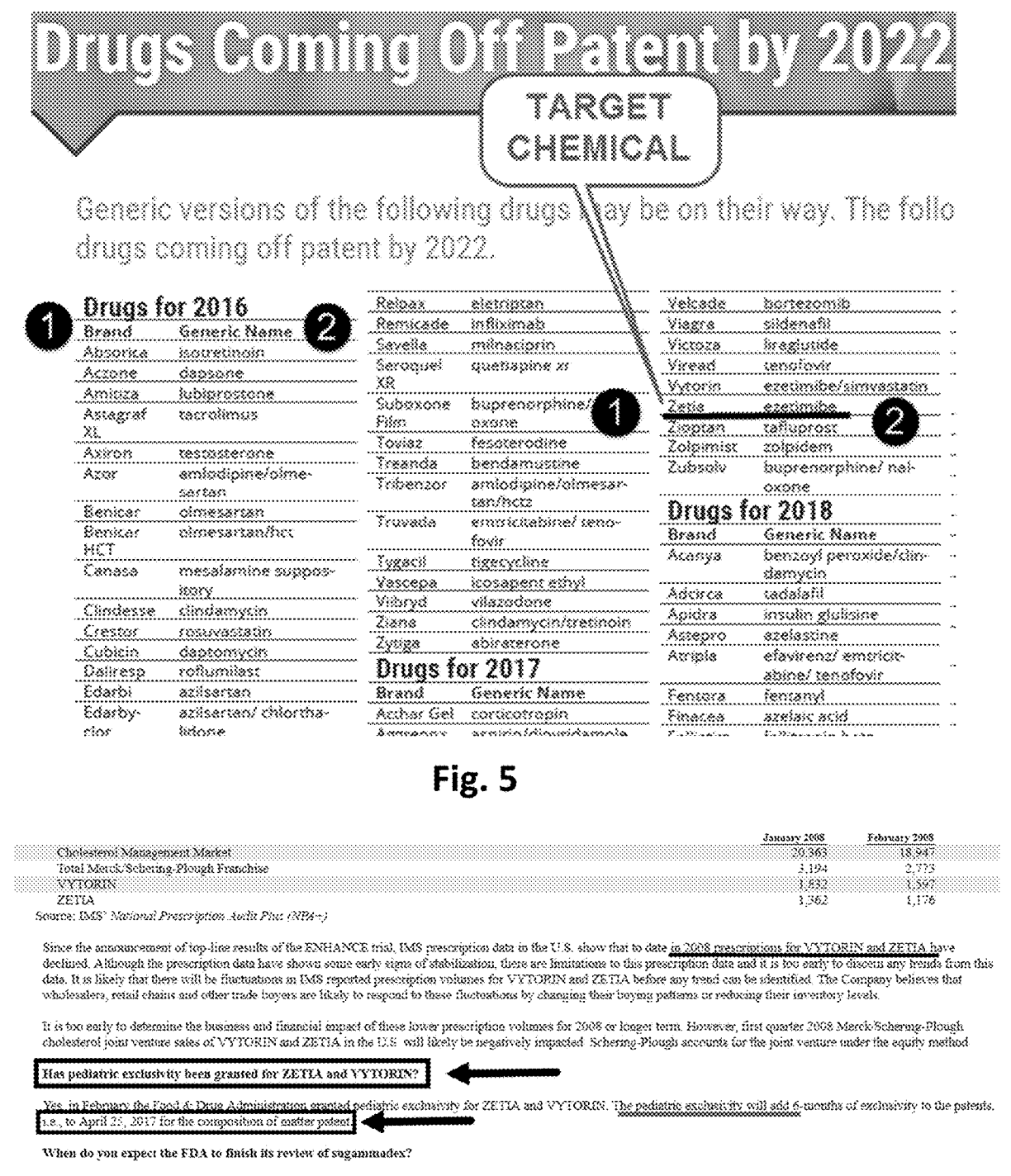

FIG. 3 is a representative excerpt of a court filing accessible through an exemplary method according to an embodiment of the disclosure. FIG. 4 is a representative excerpt of Food and Drug Administration (FDA) correspondence accessible through an exemplary method according to an embodiment of the disclosure. FIG. 5 is a representative excerpt of public information regarding drug exclusivity expiration dates accessible through an exemplary method according to an embodiment of the disclosure. FIG. 6 is a screenshot of public information reflecting regulatory approval and drug exclusivity information accessible through an exemplary method according to an embodiment of the disclosure. In the above-mentioned FIGS. 3 to 6, a legal document, an FDA correspondence, and public information regarding drug exclusivity expiration dates as well as public information reflecting regulatory approval and drug exclusivity information are exemplified. The information described above may be searched from and related to the chemical structure in the U.S. Pat. No. RE42, 461E shown in FIG. 2. These pieces of information may be searched from the data sources associated with this search system.

According to above-described FIGS. 1 to 6, the search apparatus of the embodiments of the present disclosure associates with at least one database of chemical structures involving chemical structures and at least one database of public literature involving public literature.

Figures 7, 8:
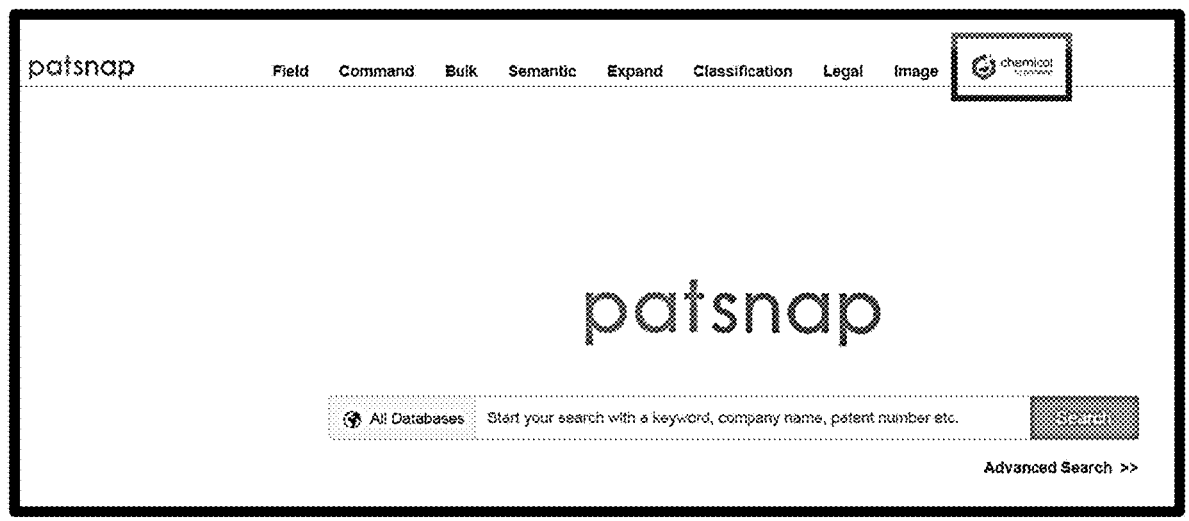
FIG. 7 is a screenshot of the Patsnap chemical tool search page according to an embodiment of the disclosure.
FIG. 8 is a screenshot excerpt of an exemplary search performed according to an embodiment of the disclosure.

FIG. 7 is a screenshot of the Patsnap chemical tool search page according to an embodiment of the disclosure. The user may go from the Patsnap Analytics system to a search page of the present Patsnap Chemical tool through the user interface of the terminal device he uses. As can be seen from FIG. 1, the Patsnap chemical tool may be linked to the Patsnap Analytics system and the Patsnap Chemscape system. The Patsnap Chemscape system is a chemical landscaping tool and is used to display map data information related to chemical structures.

Figures 9, 10:
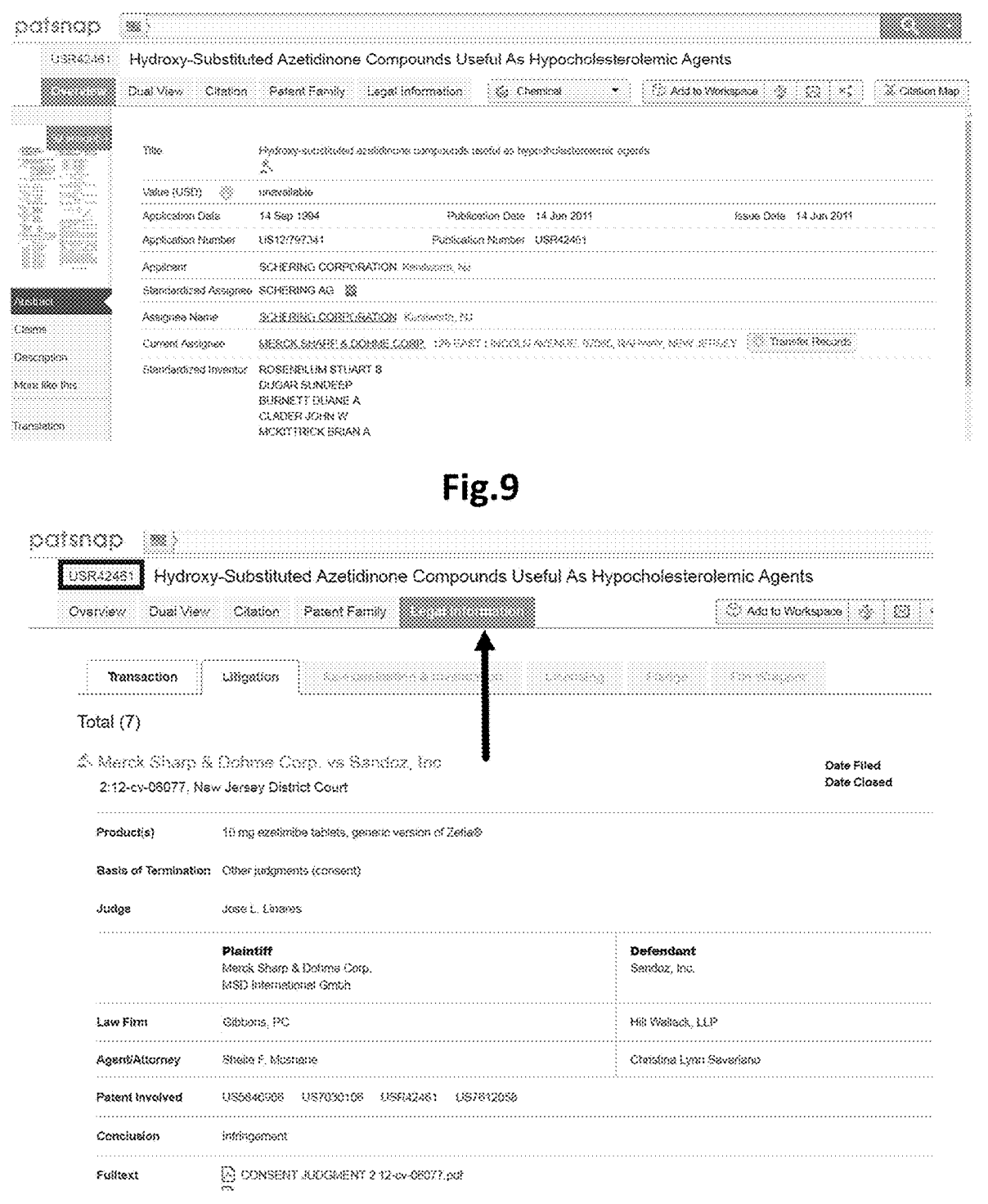
Figure 11:
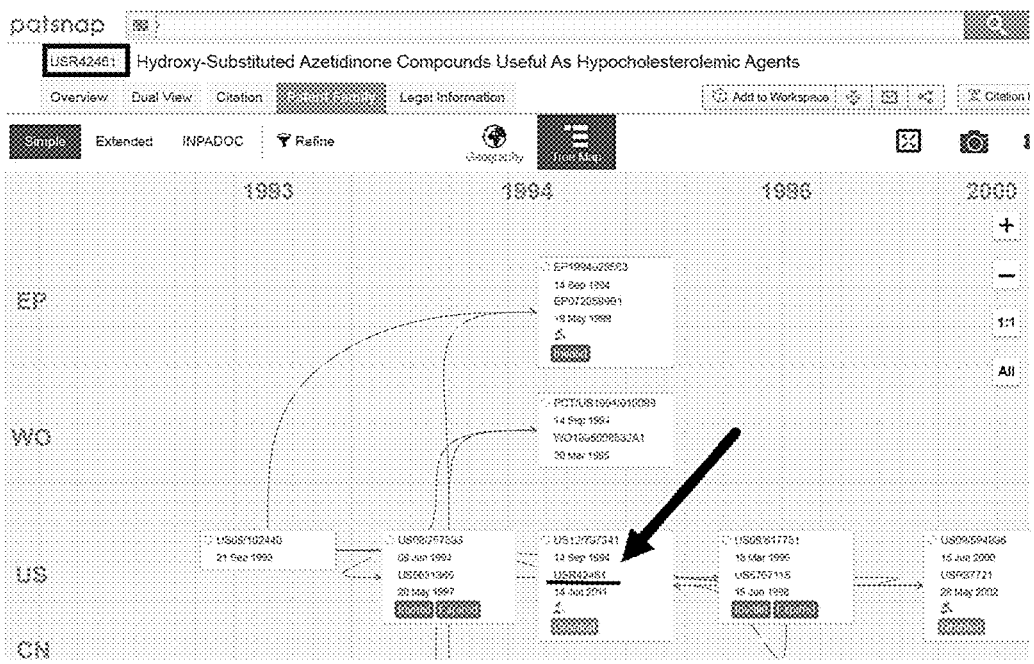
FIG. 11 is a screenshot excerpt of patent map associated with a patent family accessible through an exemplary method according to an embodiment of the disclosure.
Figure 12:
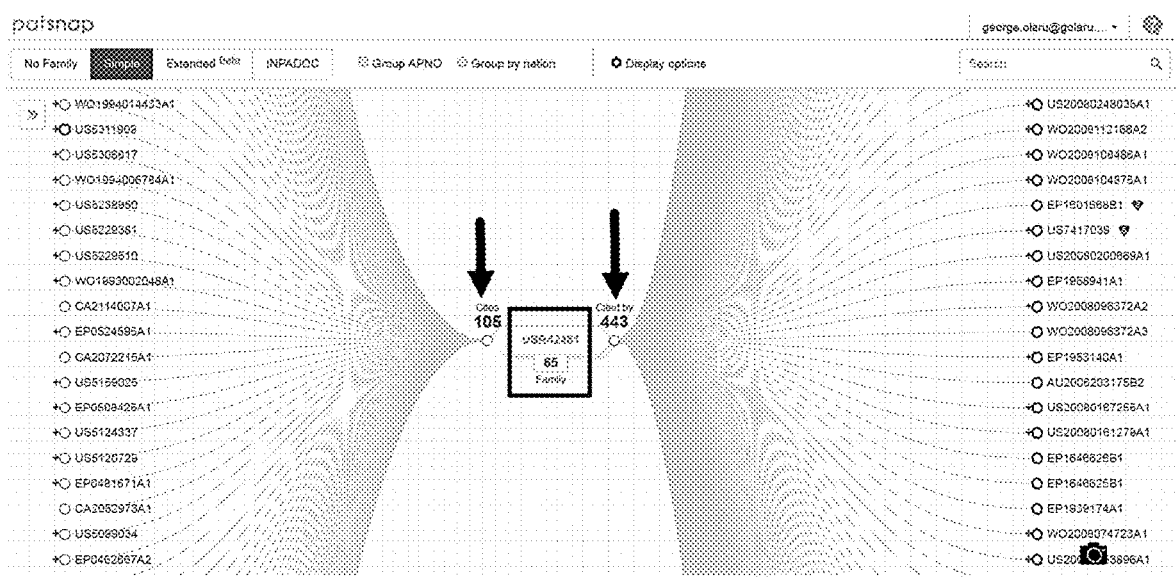
FIG. 12 is a simple patent family and patent citation map compiled through an exemplary method according to an embodiment of the disclosure.

FIGS. 8 to 12 illustrate examples of patent maps generated by the Patsnap Analytics system. FIG. 8 is a screenshot excerpt of an exemplary search performed according to an embodiment of the disclosure. For example, all of patent families of the patent may be found by searching for a patent U.S. Pat. No. 5,767,115 using the Patsnap Analytics system, and the Pat. No. U.S. R42461 is included in the patent families. FIG. 9 is a screenshot excerpt of sample patent and associated patent information accessible through an exemplary method according to an embodiment of the disclosure. Information of the Pat. No. U.S. R42461, such as patent information and an abstract, is shown in FIG. 9. FIG. 10 is a screenshot excerpt of sample legal information associated with a sample patent accessible through an exemplary method according to an embodiment of the disclosure. FIG. 11 is a screenshot excerpt of patent map associated with a patent family accessible through an exemplary method according to an embodiment of the disclosure. As shown in FIG. 11, the Patsnap Analytics system shows the relationship between patent families in a tree structure. The legal status information of all the patents may be merged in light of a simple family, an extended family, or an INPADOC family. FIG. 12 is a simple patent family and patent citation map compiled through an exemplary method according to an embodiment of the disclosure. As shown in FIG. 12, the Patsnap Analytics system shows which patents cite a patent (such as U.S. R42461), and which other patents are cited by this patent, so that the patents may be merged according to the simple family, the extended family, and the INPADOC family.

Figure 13:
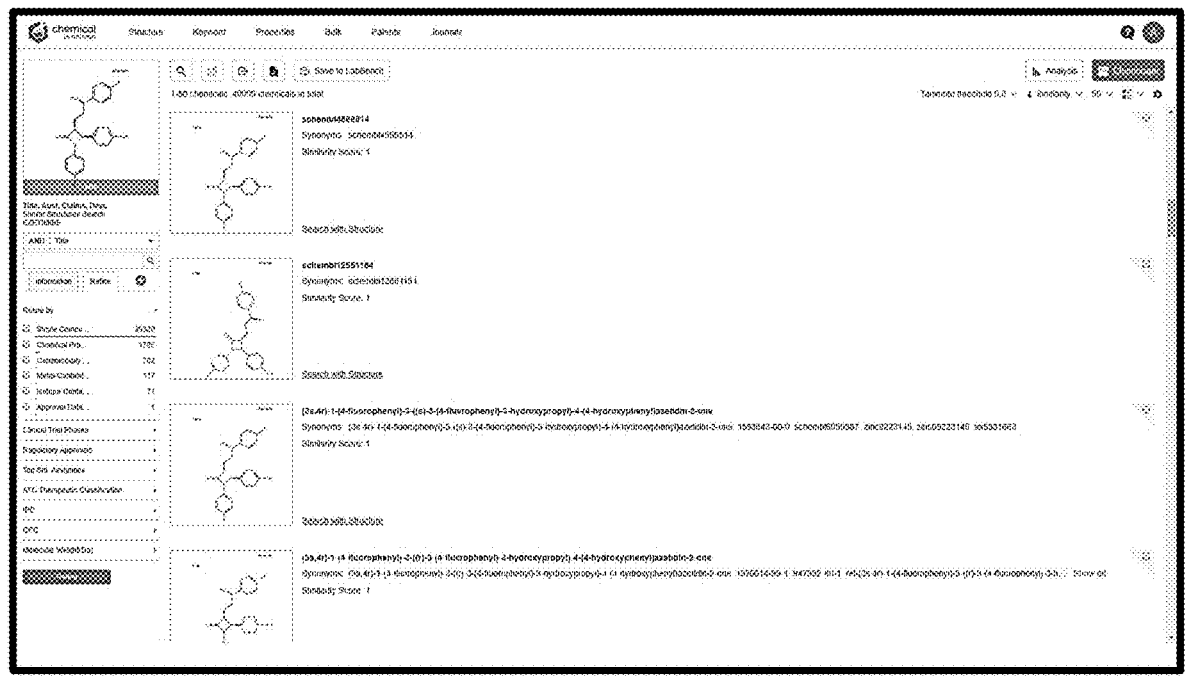
FIG. 13 is a representative excerpt of chemical structure information accessible through an exemplary method according to an embodiment of the disclosure.

FIG. 13 is a representative excerpt of chemical structure information accessible through an exemplary method according to an embodiment of the disclosure. A search page of the Patsnap Chemical for chemical structures is shown in FIG. 13. The search page may show a search result page of related chemical structures searched based on the target chemical structure on the upper left corner of the FIG. 13. For example, similar structures are searched based on the chemical structure of Zetia, and the search result page includes a structure diagram of Zetia, an alias Ezetimibe, and information such as related patent cases of similar structures of Zetia. The related patent cases include a structure diagram of a similar structure, a similarity of the similar structure and the target chemical structure Zetia, an alias of the similar structure, and a Search with Structure by using the similar structure for re-searching. The search results may also be refined according to chemical and/or patent properties in the left side column. The chemical property includes, but is not limited to, a structure type, a clinical research phase, molecular weight, ATC code, etc. The patent property includes, but is not limited to, an applicant (a patentee), an IPC classification number, a CPC classification number, etc.

Figure 14:
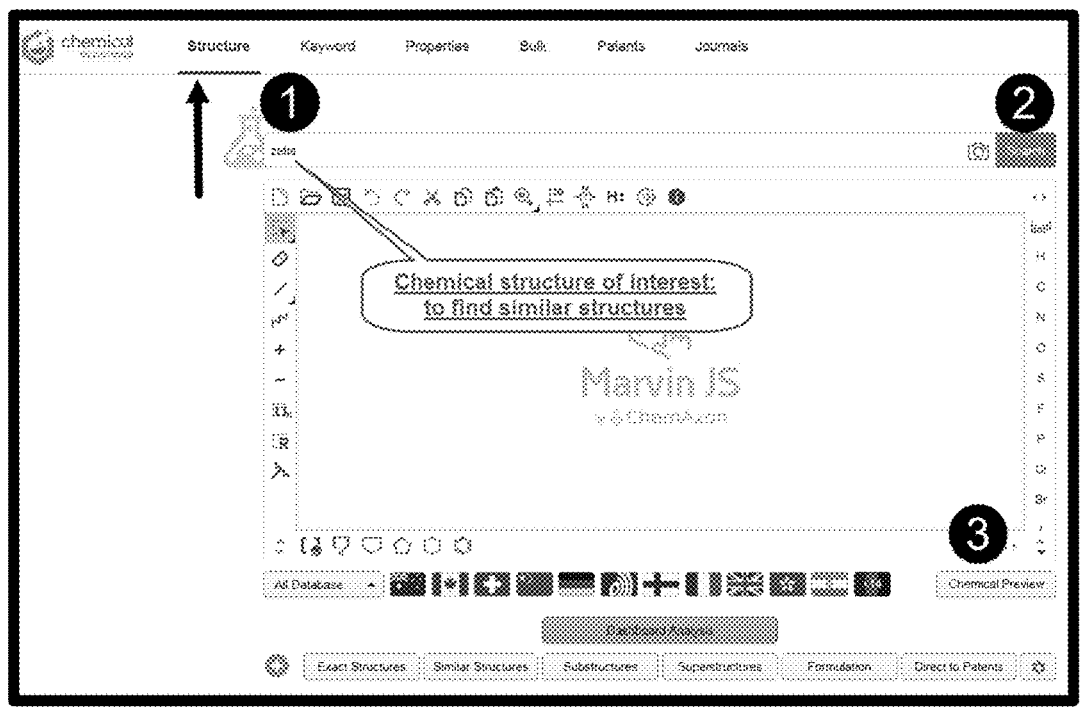
FIG. 14 is a screenshot excerpt of a chemical structure search that can be performed through an exemplary method according to an embodiment of the disclosure.

FIG. 14 is a screenshot excerpt of a chemical structure search that can be performed through an exemplary method according to an embodiment of the disclosure. A search home page of the Patsnap Chemical for chemical structures is shown in FIG. 14. First, the user may directly enter a chemical name, or upload a picture of a chemical structure formula, or may also use a structure editor to edit and/or modify a chemical structure. As entering and editing, the system may display the related information of the chemical structure stored in the system in real time as a preview.

Figure 15:
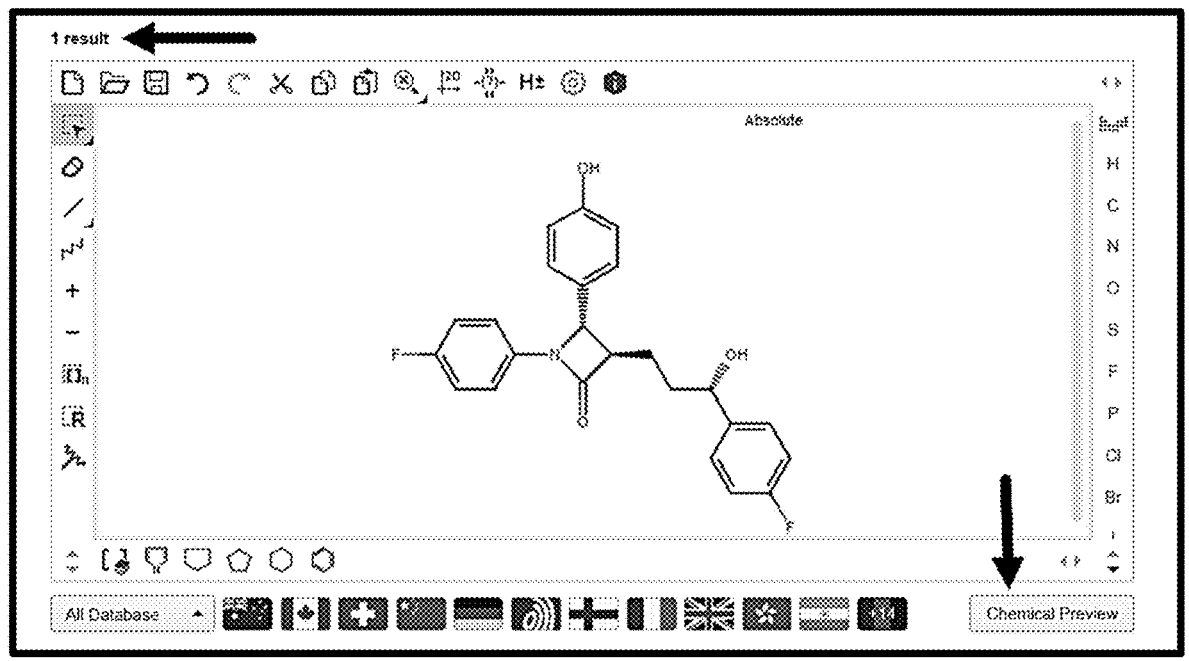
FIG. 15 is a screenshot excerpt of a chemical structure reflecting the search that was performed in FIG. 14.
Figure 16:
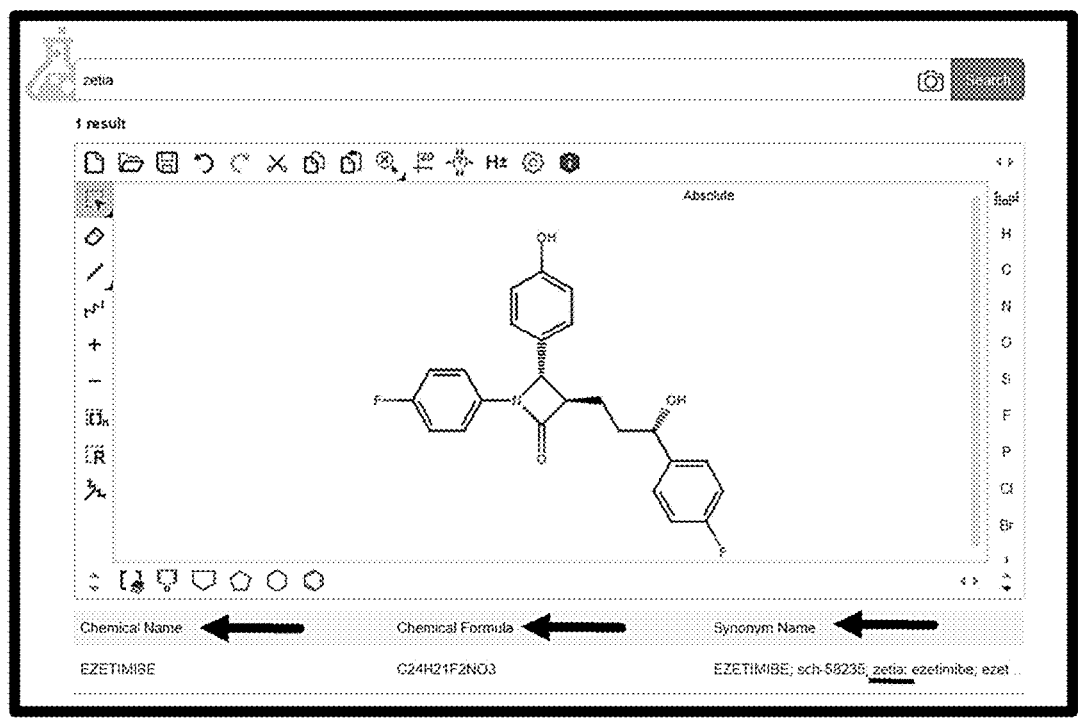
FIG. 16 is a screenshot excerpt reflecting information regarding the chemical structure search that was performed in FIG. 14.

FIG. 15 is a screenshot excerpt of a chemical structure reflecting the search that was performed in FIG. 14. FIG. 16 is a screenshot excerpt reflecting information regarding the chemical structure search that was performed in FIG. 14. As shown in FIG. 15, after entering a chemical name (such as a drug name Zetia) in the search bar of the search home page of the Patsnap Chemical for chemical structures, the structure of a compound corresponding to the input Zetia may be automatically displayed in the edit box. After a preview button in the lower right corner of FIG. 15 is clicked, related information about the compound stored in the system, such as a chemical name, an alias, a chemical formula and the like, will be shown below the screenshot of FIG. 16.

Figure 17:
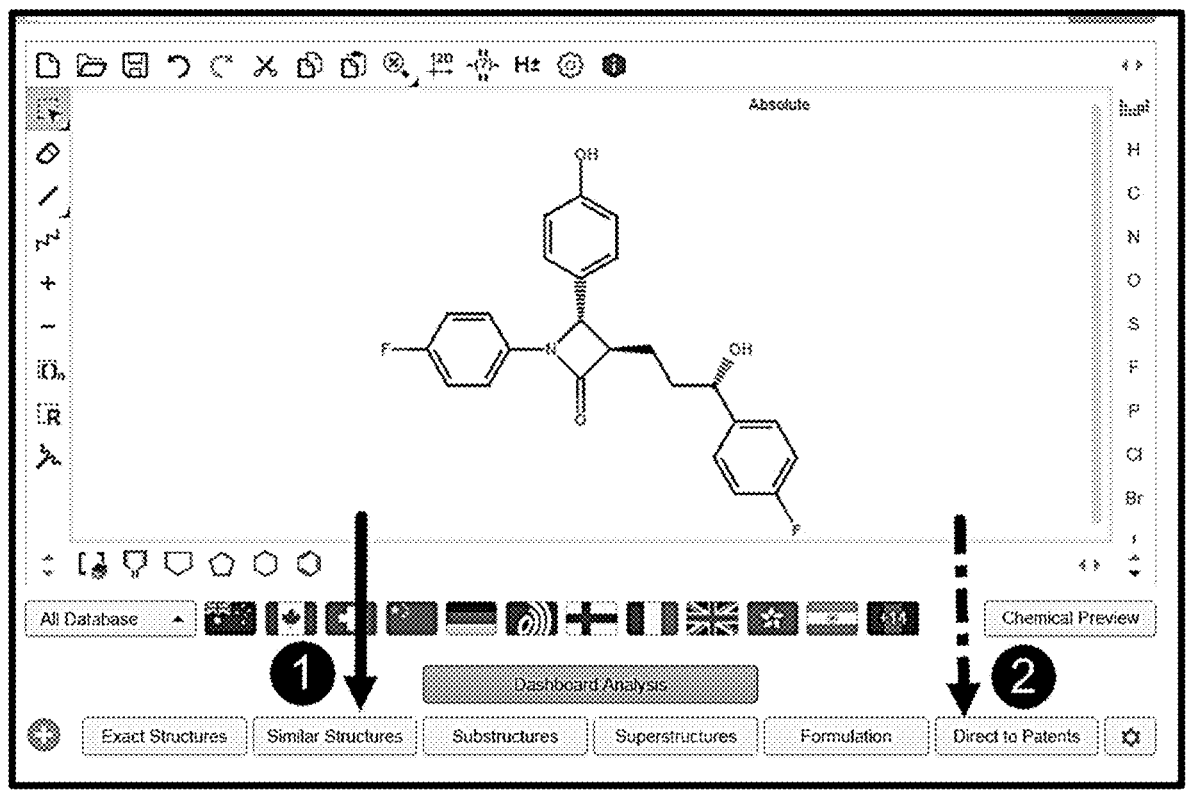
FIG. 17 is a screenshot excerpt reflecting analytical tools relating to the chemical structure reflected in FIG. 15.

FIG. 17 is a screenshot excerpt reflecting analytical tools relating to the chemical structure reflected in FIG. 15. Referring to FIG. 17, on the search home page of the Patsnap Chemical for chemical structures, a system may perform a search for related chemical structures regarding to the target chemical structure input by the user. For example, as shown below the screenshot of FIG. 17, an exact structure search, a similar structure search, a substructure search, and a superstructure search may be included, and patent documents related to the chemical structure may also be directly viewed.

Figure 18:
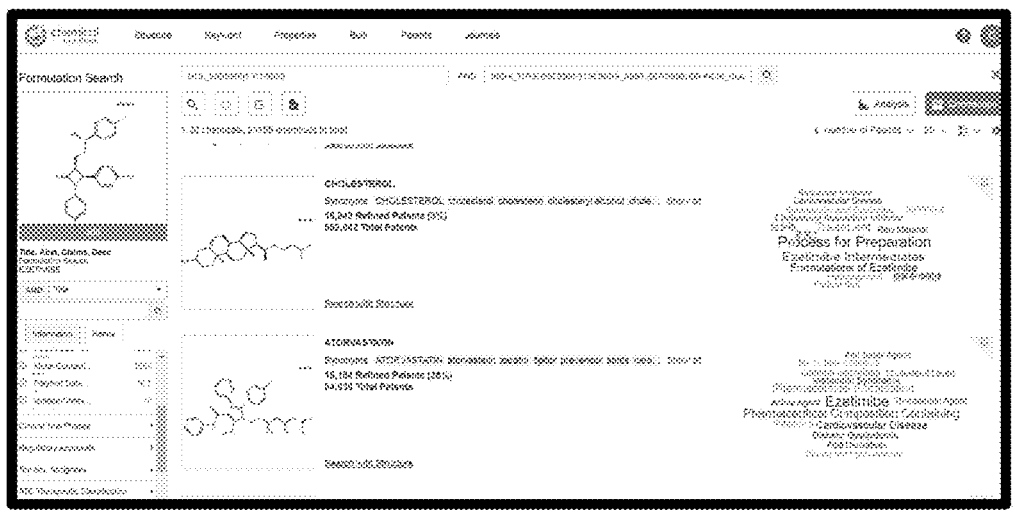
FIG. 18 is a screenshot excerpt reflecting the search performed using the analytical tools reflected in FIG. 17.

FIG. 18 is a screenshot excerpt reflecting the search performed using the analytical tools reflected in FIG. 17. A result page is shown in FIG. 18 after the similar structure search according to the chemical structural formula shown in FIG. 17. The result page includes chemical structural formulas, corresponding aliases, and associated patent cases related to the target chemical structure.

Figure 19:
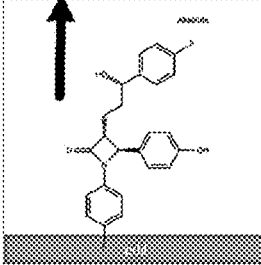
FIG. 19 is a screenshot excerpt reflecting chemical structures deemed related to the target chemical structure reflected in the search performed in FIG. 14.

FIG. 19 is a screenshot excerpt reflecting chemical structures deemed related to the target chemical structure reflected in the search performed in FIG. 14. In the screenshot shown in FIG. 19, the search results may be refined according to information such as the chemical structure and/or the patent property. That is, the chemical structure or the patent information of interest may be refined. For example, a formulation search is performed in FIG. 14, 21,155 search results that include all patents of components constituting a chemical substance together with Ezetimibe are obtained, and the patent situation relating to each of these components is shown. Then, the search results are refined in a manner of molecular weight and title plus abstract. For example, for a component Cholesterol which constitutes the chemical substance together with Ezetimibe, the search results are refined in the manner of molecular weight and title plus abstract. There are 18,943 results are the exact results after refining according to the molecular weight, the title and the abstract, which account for 3% of 662,942 results related to the Cholesterol searched according to the formulation.

Figure 20:
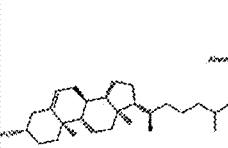
FIG. 20 is a screenshot excerpt reflecting a patent literature search with the chemical structure reflected in FIG. 16.
Figure 21:
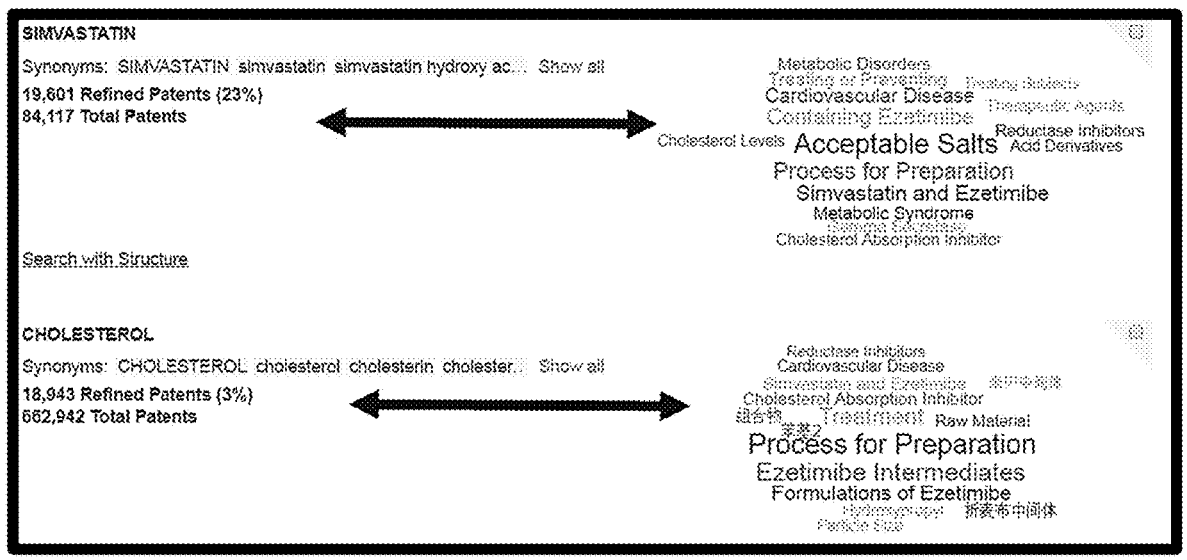
FIG. 21 is a screenshot excerpt reflecting the results of the patent literature search in FIG. 20.

FIG. 20 is a screenshot excerpt reflecting a patent literature search with the chemical structure reflected in FIG. 16. As shown in FIG. 20, after searching for the chemical structural formula shown in FIG. 16, a total of 22,442 related documents were searched, and a keyword cloud extracted from these related patents is displayed on the right side of the page, so that a secondary search may be performed according to one or more keywords from the keyword cloud, and results are shown in FIG. 21. FIG. 21 is a screenshot excerpt reflecting the results of the patent literature search in FIG. 20. The results are obtained by using a natural language processing technique to extract the keyword cloud.

Figure 22:
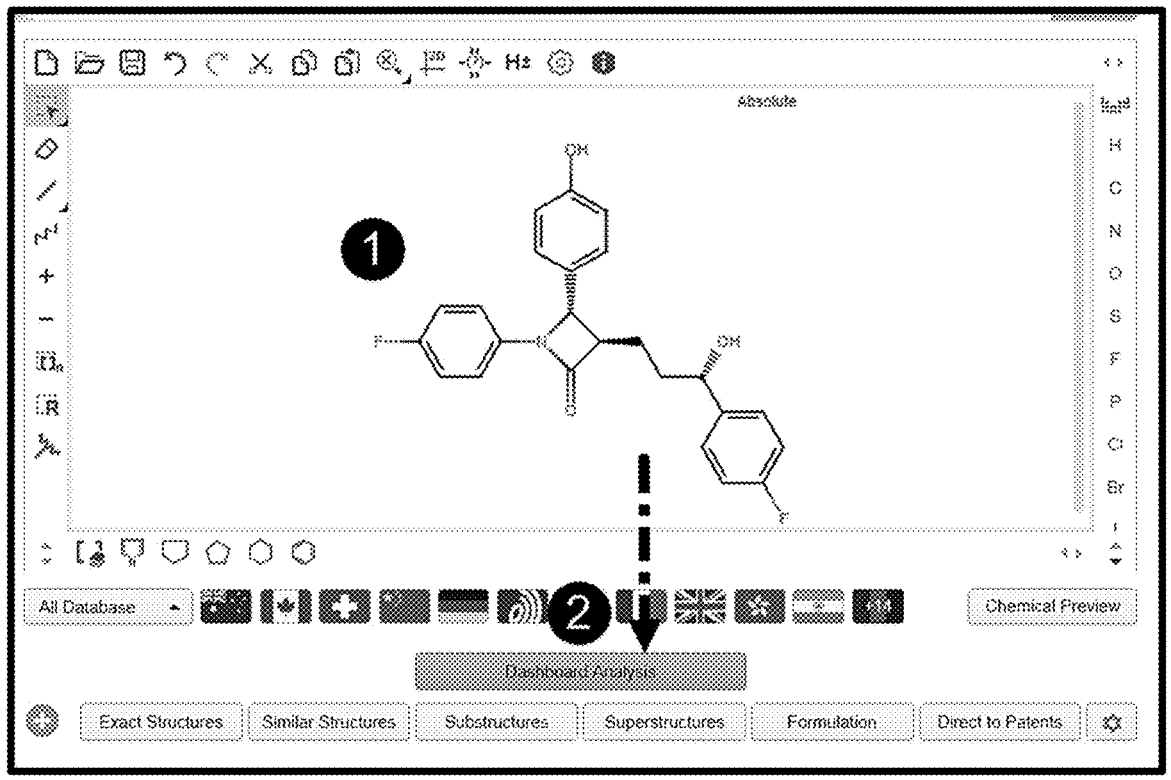
FIG. 22 is a representative excerpt of chemical structure information accessible through an exemplary method according to an embodiment of the disclosure.
Figure 23:
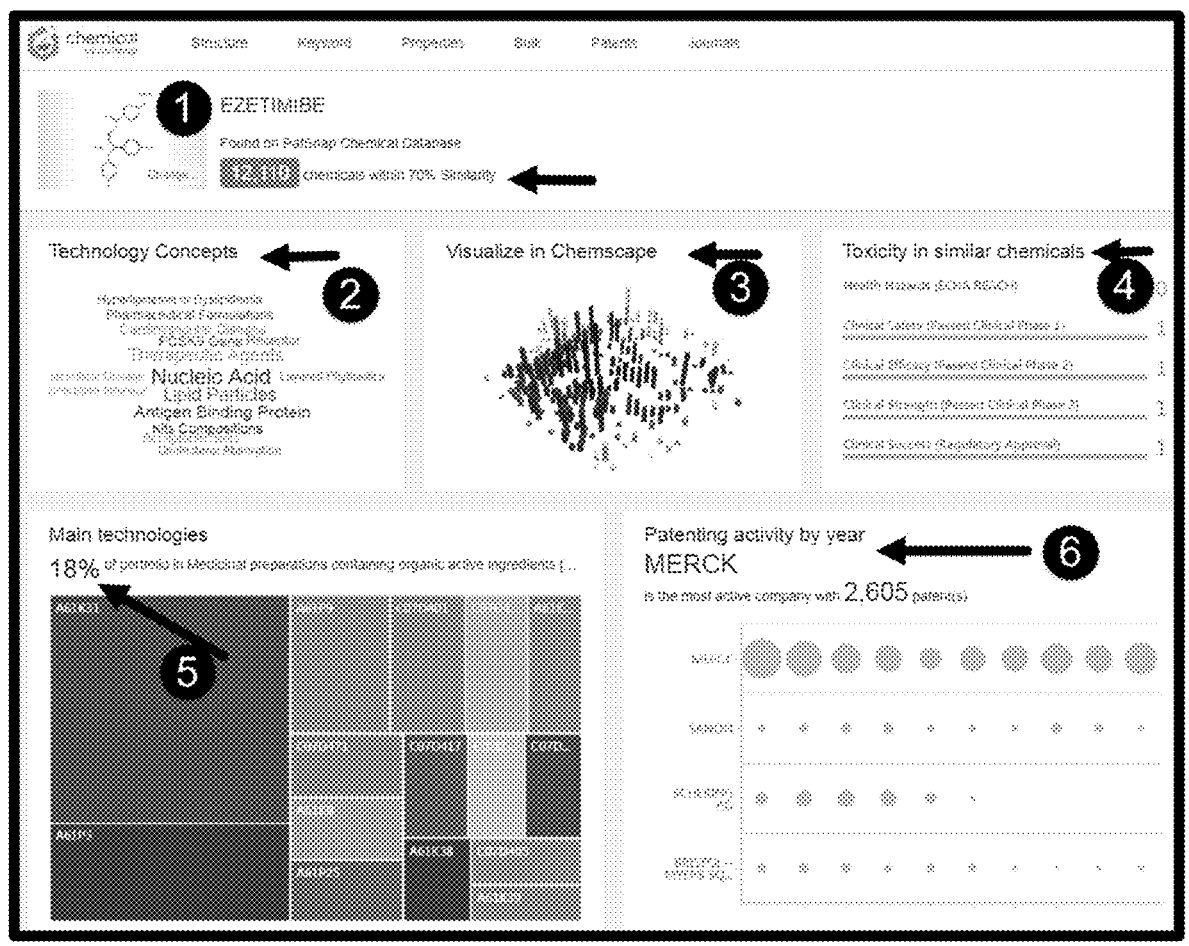
FIG. 23 is a screenshot excerpt reflecting various analytical tools and data summaries accessible through an exemplary method according to an embodiment of the disclosure.

FIG. 22 is a representative excerpt of chemical structure information accessible through an exemplary method according to an embodiment of the disclosure. As shown in FIG. 22, on the search home page of the Patsnap Chemical for chemical structures, a Dashboard Analysis corresponding to the target chemical structure queried by the user may be generated with one click. FIG. 23 is a screenshot excerpt reflecting various analytical tools and data summaries accessible through an exemplary method according to an embodiment of the disclosure. The various analysis tools and data summaries shown in FIG. 23 are displayed by clicking the one-click generation bottom, Dashboard Analysis, in FIG. 22. The analysis tools and data summaries may include: basic information about the searched chemical structure, the number of associated patents, keyword clouds of associated patents, a 3D-map of the similar chemical structures, toxicity in similar compounds, an IPC disclosure of associated patents, patent rankings of associated companies and annual trends thereof, etc.

Figure 24:
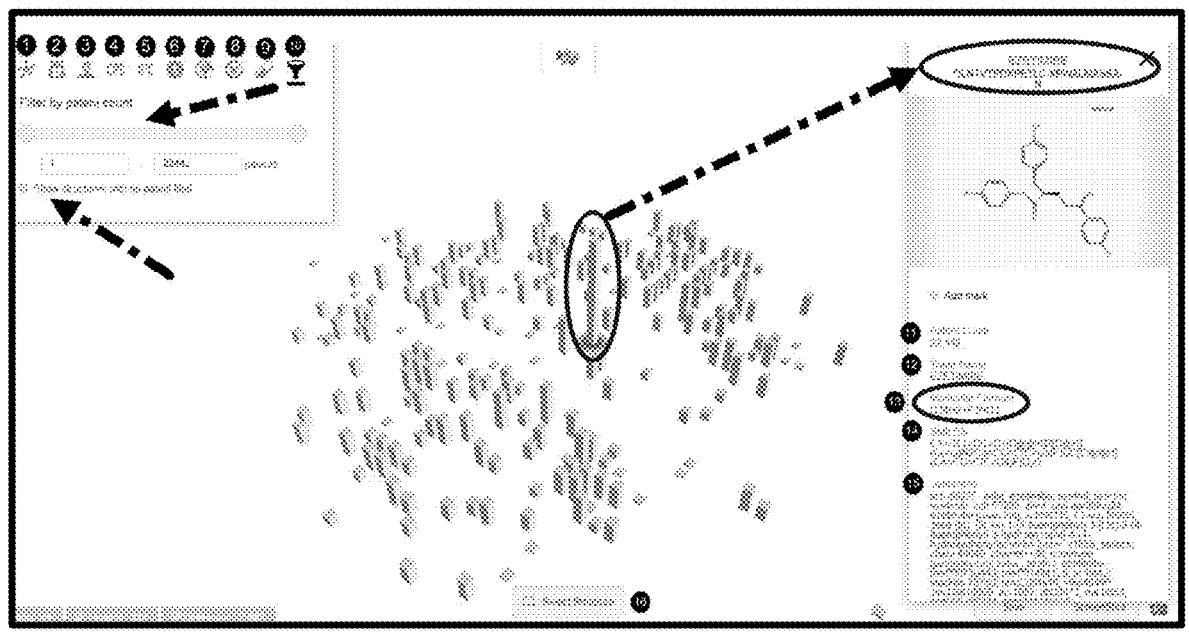
FIG. 24 is a screenshot excerpt reflecting a three dimensional model of chemical structures accessible through an exemplary method according to an embodiment of the disclosure.

FIG. 24 is a screenshot excerpt reflecting a three dimensional model of chemical structures accessible through an exemplary method according to an embodiment of the disclosure. As shown in FIG. 24, the 3D-map shows the number of related patents of chemical structures related to the searched target chemical structure. In the FIG. 24, each column represents a chemical structure, the height of the column is the number of patents of the chemical structure, and the selected chemical structure may be supported to be refined in the 3D-map.

Figure 25:
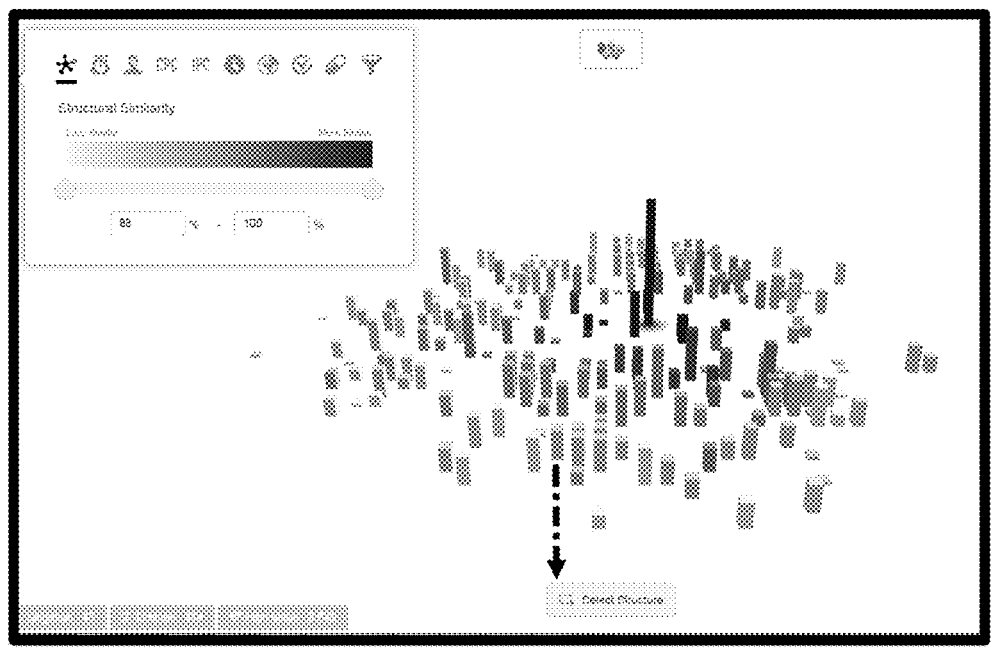
FIG. 25 is a screenshot excerpt reflecting an analytical tool regarding analysis of chemical structures reflected in a three-dimensional model accessible through an exemplary method according to an embodiment of the disclosure.

FIG. 25 is a screenshot excerpt reflecting an analytical tool regarding analysis of chemical structures reflected in a three-dimensional model accessible through an exemplary method according to an embodiment of the disclosure. As shown in FIG. 25, the 3D-map shows the similarity between the related chemical structures and the target chemical structure. As shown in the FIG. 25, the color of the column represents the similarity of the chemical structures. The deeper the color of the column is, the higher the similarity between the chemical structure represented by the column and the target chemical structure queried by the user is; and the shallower the color of the column is, the lower the similarity between the chemical structure represented by the column and the target chemical structure queried by the user is.

Figure 26:
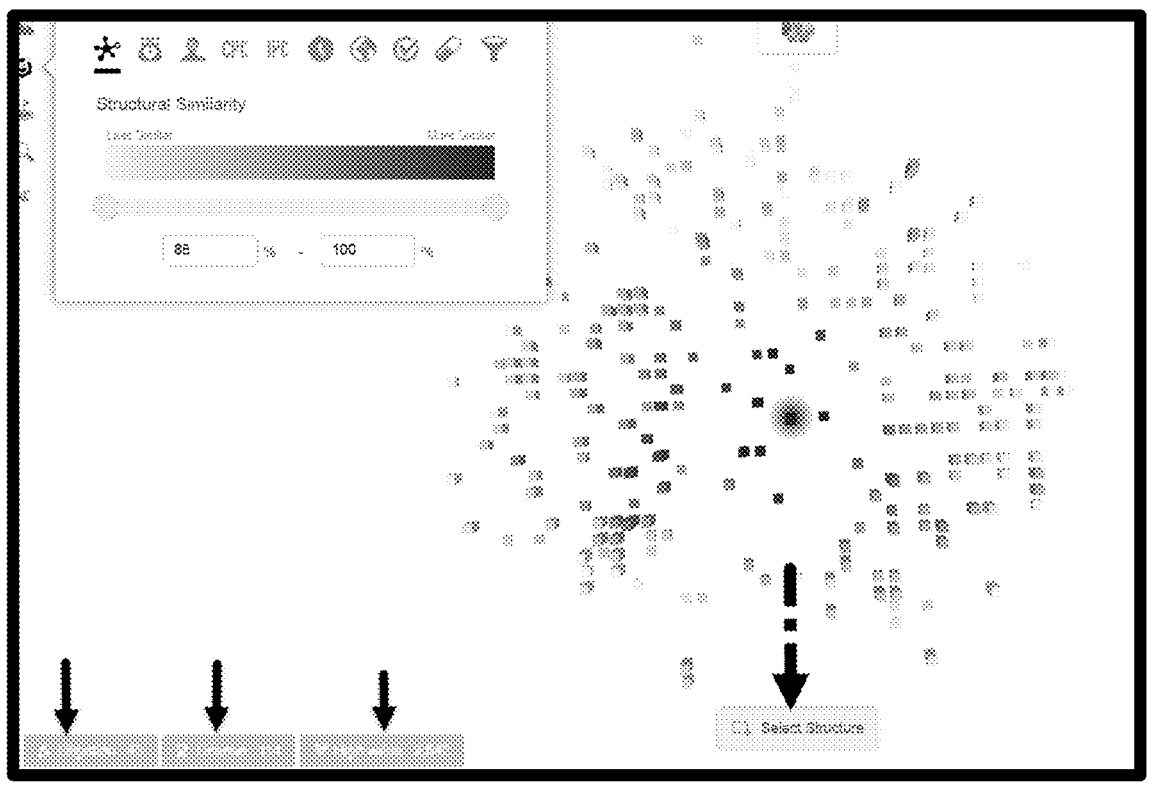
FIG. 26 is a screenshot excerpt reflecting a two-dimensional model of chemical structures accessible through an exemplary method according to an embodiment of the disclosure.

FIG. 26 is a screenshot excerpt reflecting a two-dimensional model of chemical structures accessible through an exemplary method according to an embodiment of the disclosure. As shown in FIG. 26, the 3D-map shown in FIG. 25 may also be converted into a 2D-map mode. The 2D-map also shows some pieces of patent information of patents relating to the related chemical structures, such as litigation information, license information, and patent value information.

Figure 27:
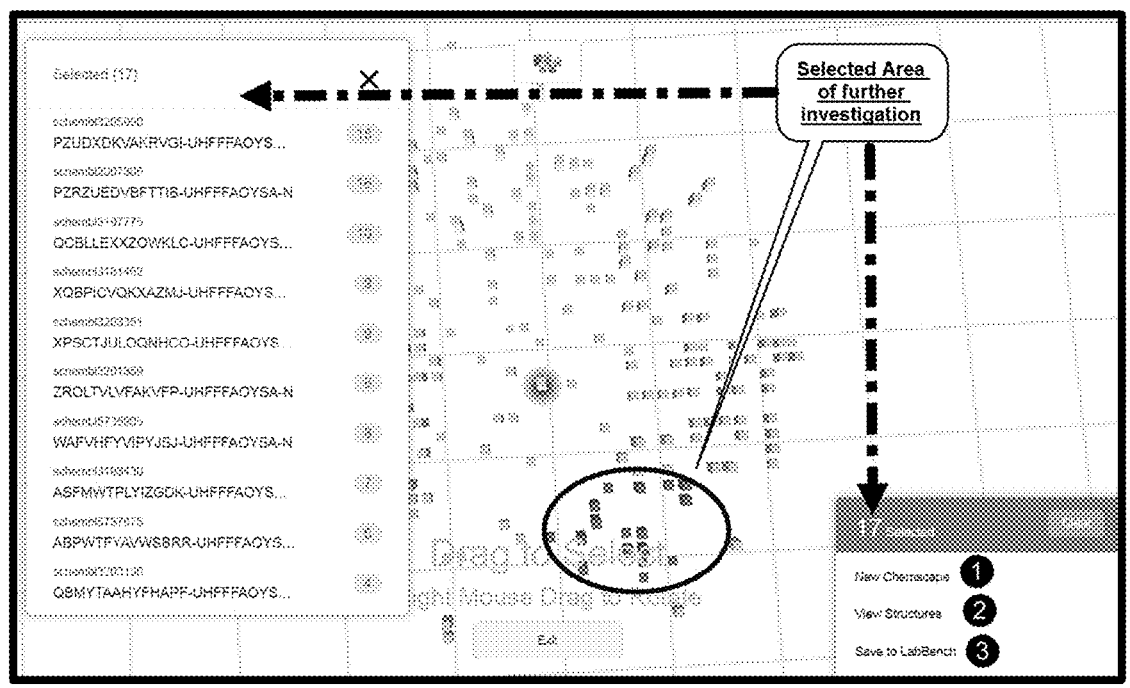
FIG. 27 is a screenshot excerpt reflecting an analytical tool relating to analysis of a collection of similar chemical structures accessible through an exemplary method according to an embodiment of the disclosure.
Figures 28, 29:
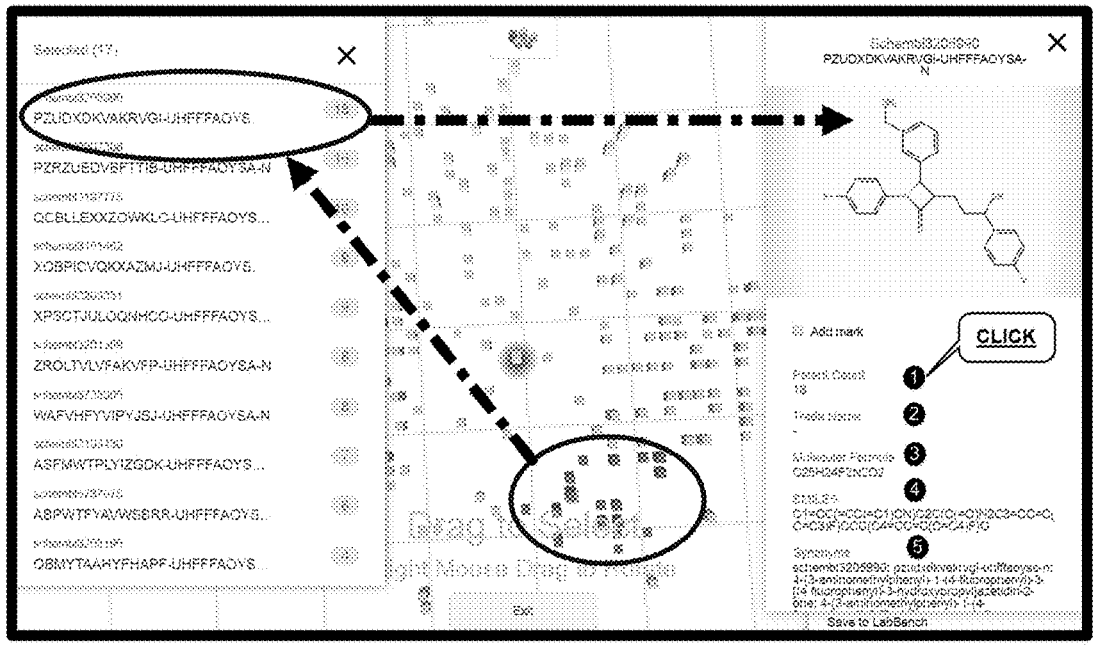
FIG. 28 is a screenshot excerpt reflecting a listing of grouped chemical structures and associated patent and chemical structure information relating to analysis of a collection of similar chemical structures accessible through an exemplary method according to an embodiment of the disclosure.
FIG. 29 is a screenshot excerpt reflecting patent related information associated with a group of chemical structures accessible through an exemplary method according to an embodiment of the disclosure.

FIG. 27 is a screenshot excerpt reflecting an analytical tool relating to analysis of a collection of similar chemical structures accessible through an exemplary method according to an embodiment of the disclosure. FIG. 28 is a screenshot excerpt reflecting a listing of grouped chemical structures and associated patent and chemical structure information relating to analysis of a collection of similar chemical structures accessible through an exemplary method according to an embodiment of the disclosure. In an embodiment, the circled area in FIG. 27 may be selected for further investigation. At this point, a list will appear on the left side of the page showing the related chemical structures in the circled area, and the selected related chemical structures may be further analyzed. As shown in the lower right of FIG. 27, for the selected related chemical structures, a new map may be created, and then displaying and analyzing, viewing structures or saving to LabBench may be performed on the new map. As shown in FIG. 28, when a related chemical structure of interest is selected, the structural formula, the chemical name, the number of patents and the like of the selected chemical structure are displayed on the right side of the page. When the number of patents displayed on the right side is clicked, specific patents may also be viewed.

FIG. 29 is a screenshot excerpt reflecting patent related information associated with a group of chemical structures accessible through an exemplary method according to an embodiment of the disclosure. As shown in FIG. 29, when clicking on a button, Patent Count, shown in FIG. 28, the page will go to a patent search results page of Patsnap Analytics, in which detailed patent information may be displayed, including a patent number, a legal status, a patent title, a patentee, an application date, a patent family and other information. At the same time, these patents may be further analyzed, such as advanced analysis charts in various dimensions, patent 3D-map analysis, and Insights reports of business intelligence.

Figure 30:
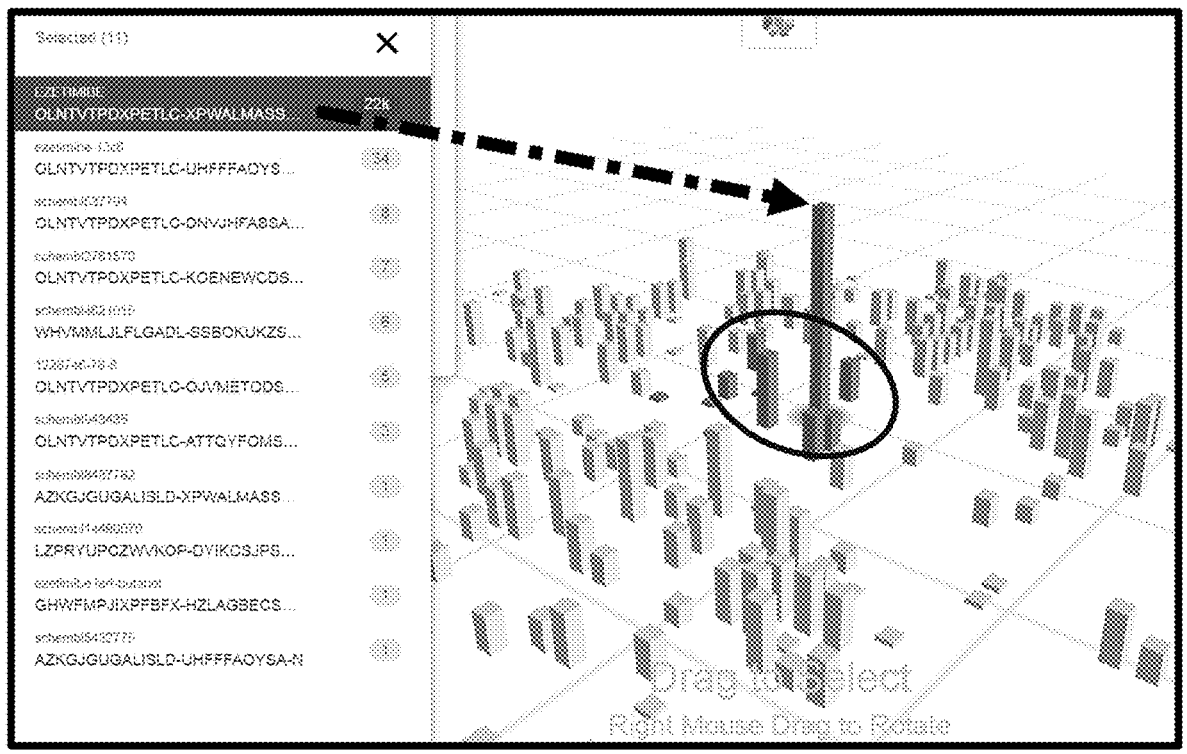
FIG. 30 is a screenshot excerpt reflecting a three-dimensional model of chemical structures and associated chemical structure identification information accessible through an exemplary method according to an embodiment of the disclosure.
Figure 31:
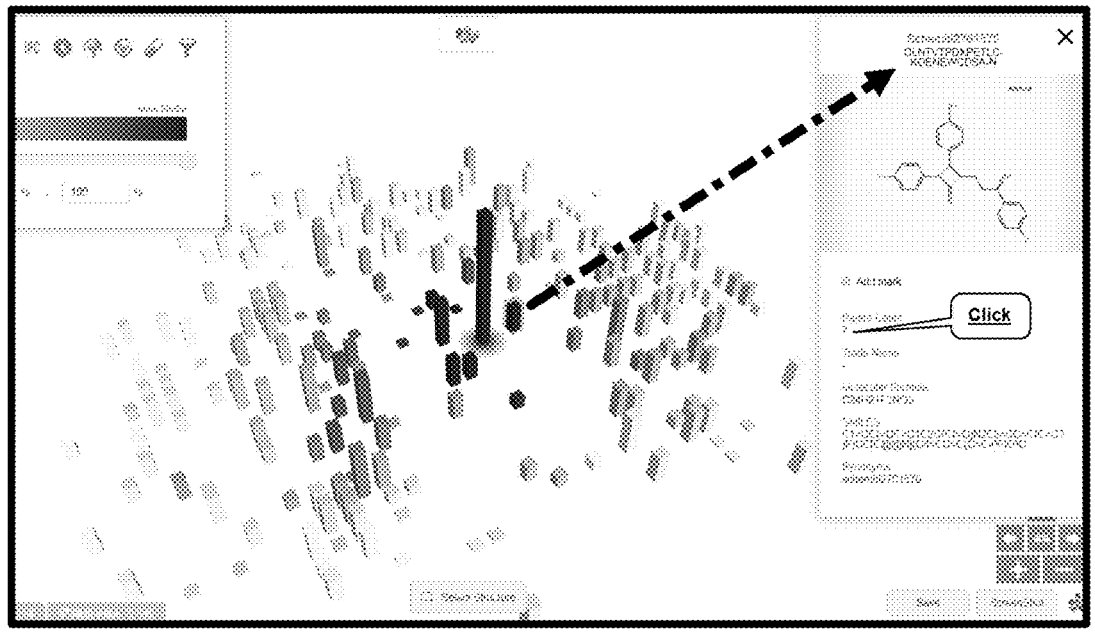
FIG. 31 is a screenshot excerpt reflecting a three-dimensional model of chemical structures and associated chemical structure identification and patent information accessible through an exemplary method according to an embodiment of the disclosure.
Figure 32:
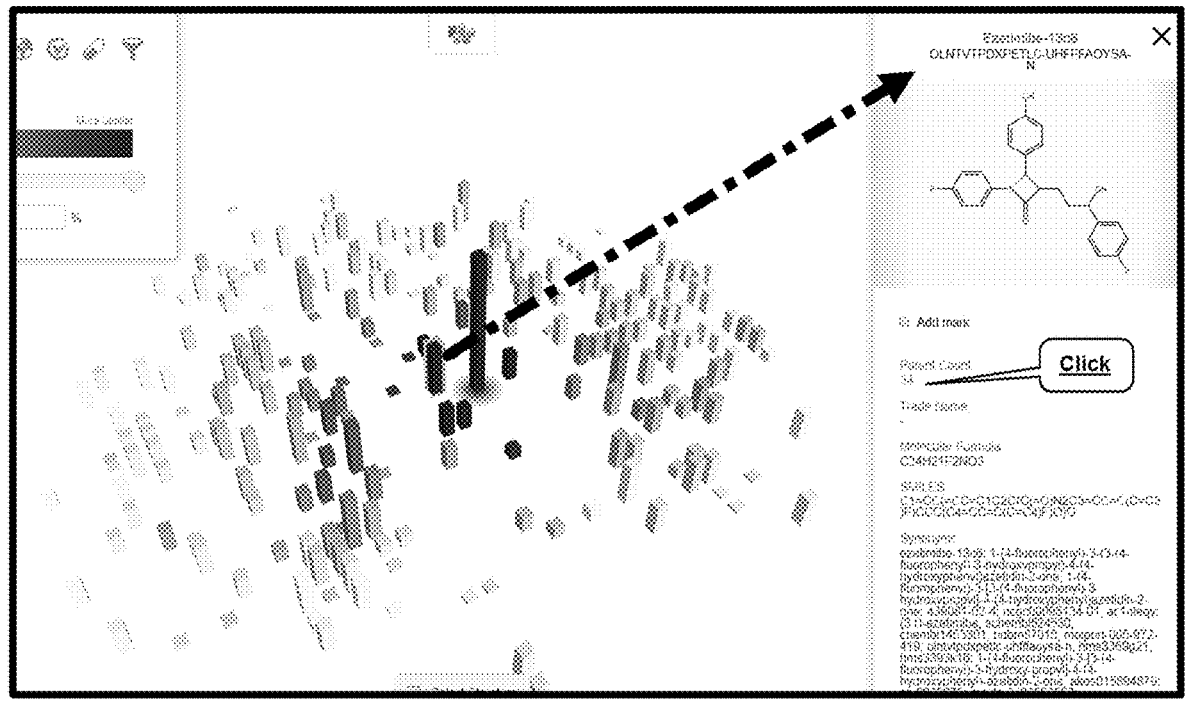
FIG. 32 is a screenshot excerpt reflecting a three-dimensional model of chemical structures reflecting a listing of grouped chemical structures and associated chemical structure identification and patent information accessible through an exemplary method according to an embodiment of the disclosure.

FIG. 30 is a screenshot excerpt reflecting a three-dimensional model of chemical structures and associated chemical structure identification information accessible through an exemplary method according to an embodiment of the disclosure. FIG. 31 is a screenshot excerpt reflecting a three-dimensional model of chemical structures and associated chemical structure identification and patent information accessible through an exemplary method according to an embodiment of the disclosure. FIG. 32 is a screenshot excerpt reflecting a three-dimensional model of chemical structures reflecting a listing of grouped chemical structures and associated chemical structure identification and patent information accessible through an exemplary method according to an embodiment of the disclosure. As shown in FIG. 30, when one of the chemical structures listed on the left side is clicked, 3D columns corresponding to this chemical structure will be highlighted in the map, which is circled in the FIG. 30. When a certain 3D column within the circled range is clicked, the structure information and patent information of the corresponding chemical structure may be displayed, as shown in FIGS. 31 and 32. It can be seen from the figures that the shorter the distance between one searched chemical structure and the target chemical structure queried by the user is, the higher their similarity is.

Figure 33:
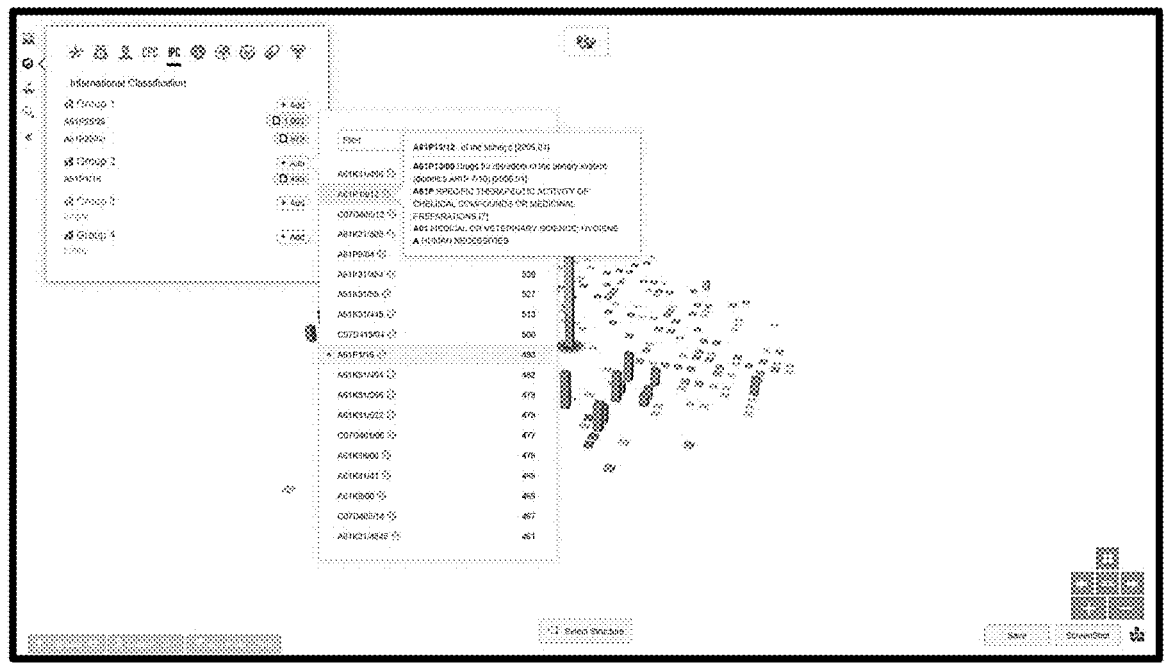
FIG. 33 is a screenshot excerpt reflecting patent grouping information, regulatory approval information, and patent classification information accessible through an exemplary method according to an embodiment of the disclosure.
Figure 34:
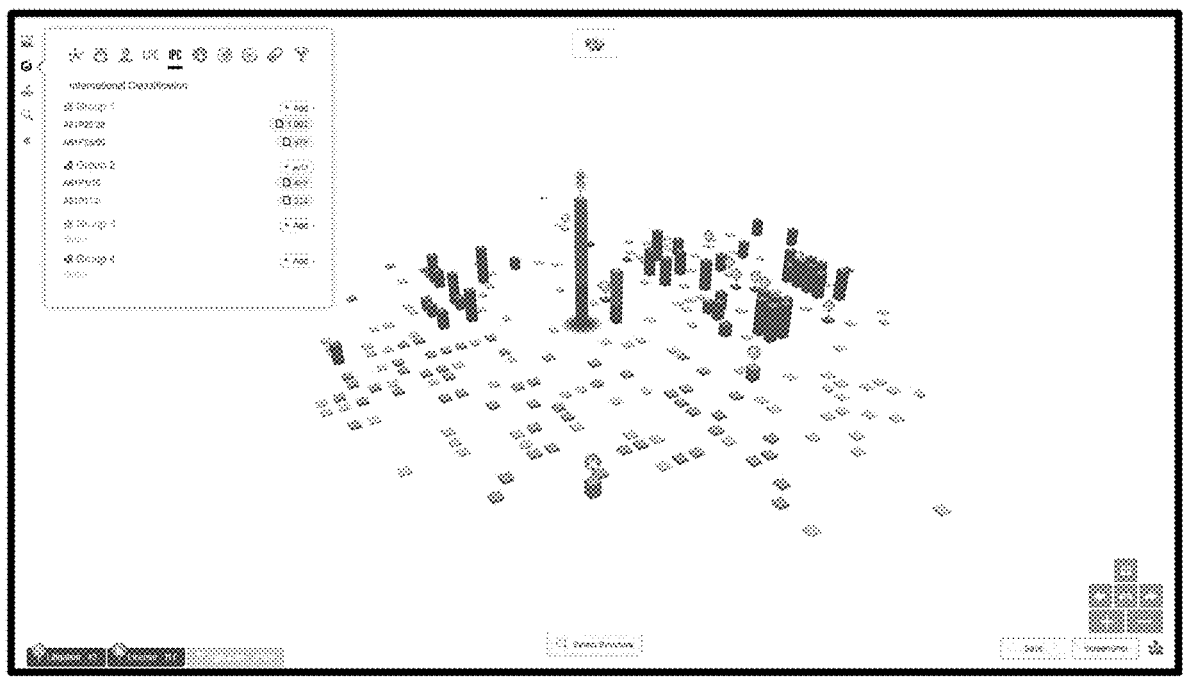
FIG. 34 is a screenshot excerpt reflecting a three-dimensional model of chemical research structures reflecting a listing of international classification groups for related chemical structures accessible through an exemplary method according to an embodiment of the disclosure.

FIG. 33 is a screenshot excerpt reflecting patent grouping information, regulatory approval information, and patent classification information accessible through an exemplary method according to an embodiment of the disclosure. FIG. 34 is a screenshot excerpt reflecting a three-dimensional model of chemical research structures reflecting a listing of international classification groups for related chemical structures accessible through an exemplary method according to an embodiment of the disclosure. In the displayed 3D-map, the search results may be further grouped based on IPC for performing a search of secondary data sets.

Figure 35:
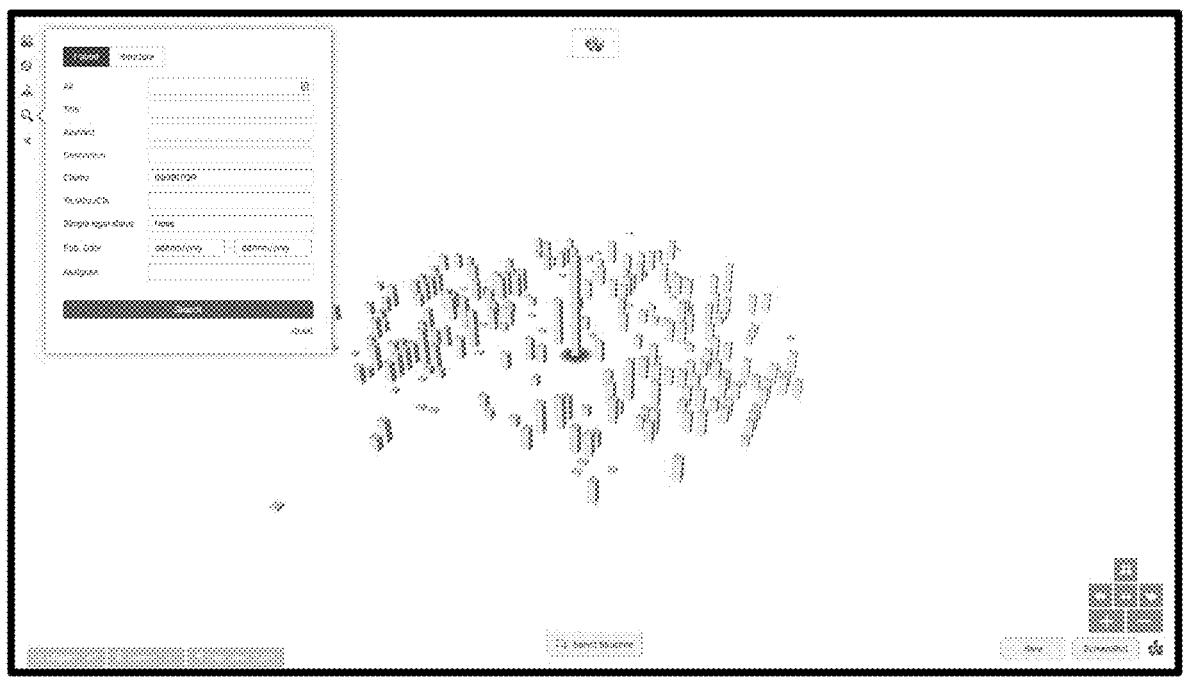
FIG. 35 is a screenshot excerpt reflecting a three-dimensional model of chemical structures and a patent search menu accessible through an exemplary method according to an embodiment of the disclosure.
Figure 36:
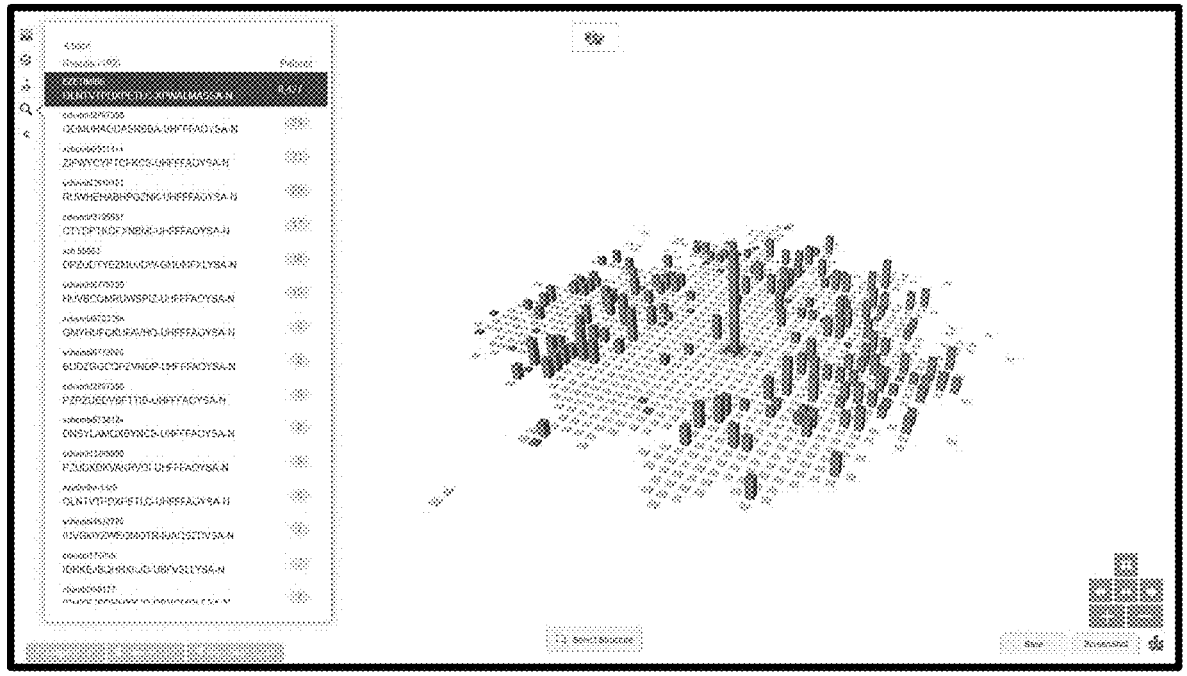
FIG. 36 is a screenshot excerpt reflecting the results of a patent search result accessible through an exemplary method according to an embodiment of the disclosure.

FIG. 35 is a screenshot excerpt reflecting a three-dimensional model of chemical structures and a patent search menu accessible through an exemplary method according to an embodiment of the disclosure. FIG. 36 is a screenshot excerpt reflecting the results of a patent search result accessible through an exemplary method according to an embodiment of the disclosure. As shown in figures, the Patsnap Chemical also supports the secondary search based on the patent information. That is, the secondary data set may include: a patent name, an abstract, a specification, claims, a legal status, a publication date, a patentee, and other information.

Figure 37:
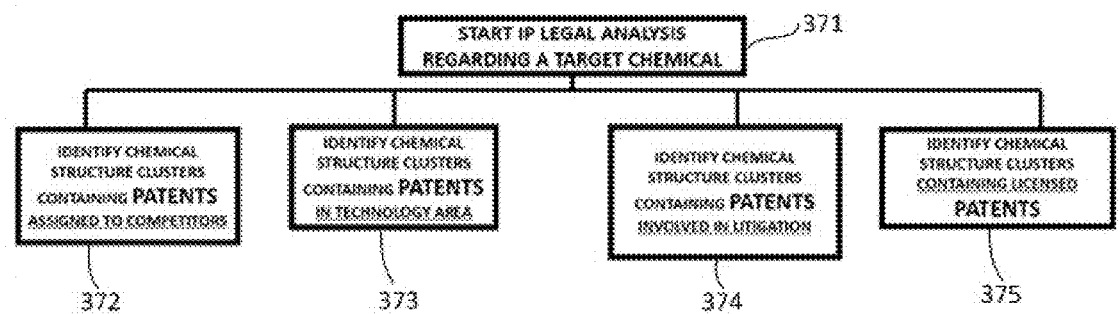
FIG. 37 is a chart reflecting various exemplary search operations and methodologies that can be used with an exemplary method according to an embodiment of the disclosure.

FIG. 37 is a chart reflecting various exemplary search operations and methodologies that can be used with an exemplary method according to an embodiment of the disclosure. The FIG. 37 illustrates an example of a user search workflow of the Patsnap Analytics system.

Figure 38:
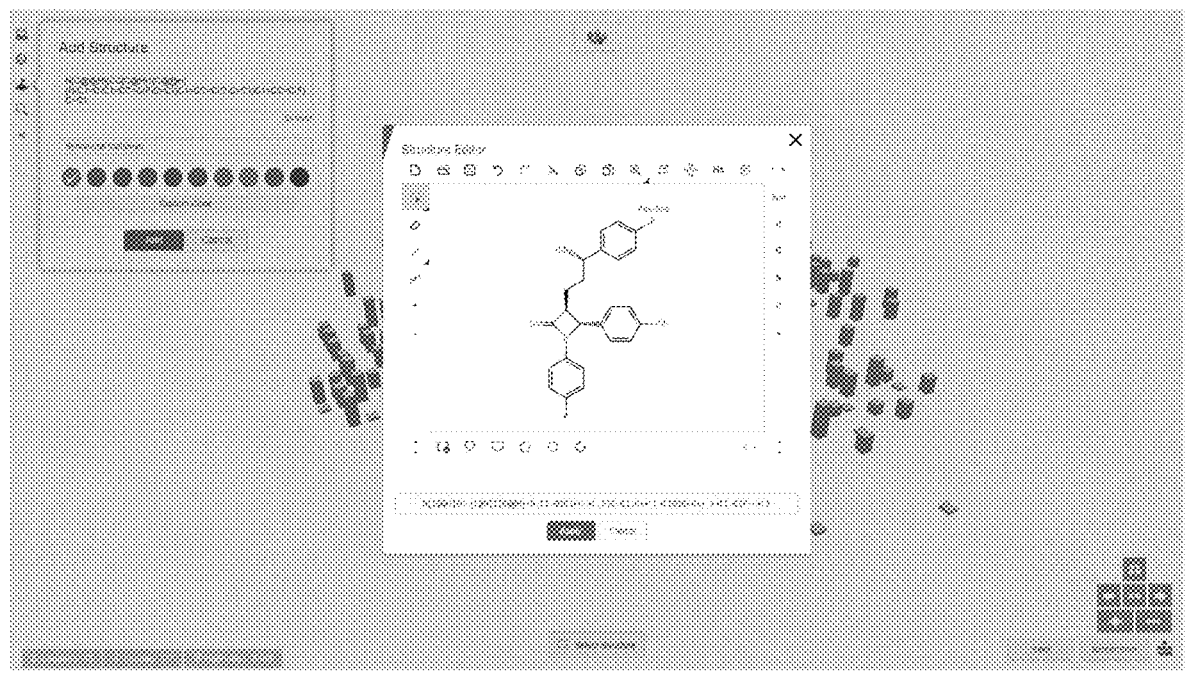
FIG. 38 is a screenshot excerpt reflecting a structure editor accessible through an exemplary method according to an embodiment of the disclosure.
Figure 39:
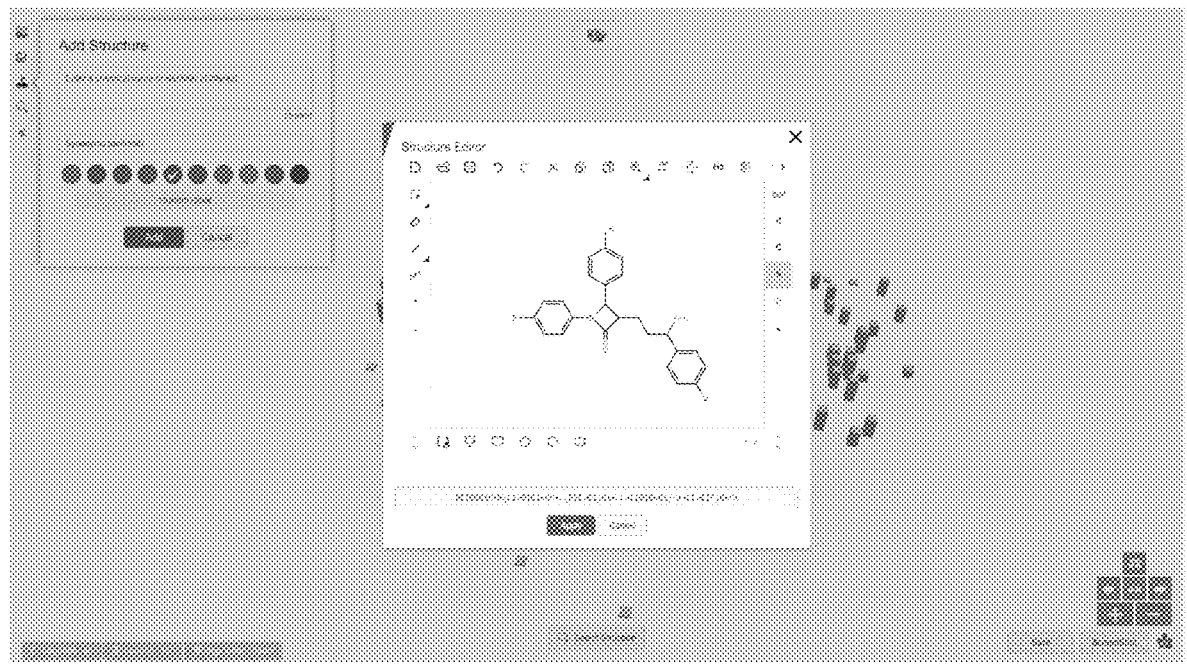
FIG. 39 is a screenshot excerpt reflecting a structure editor and an additional structure analysis tools accessible through an exemplary method according to an embodiment of the disclosure.

FIG. 38 is a screenshot excerpt reflecting a structure editor accessible through an exemplary method according to an embodiment of the disclosure. FIG. 39 is a screenshot excerpt reflecting a structure editor and an additional structure analysis tools accessible through an exemplary method according to an embodiment of the disclosure. As shown in figures, on the generated 3D-map, the user is further allowed to further enter the name of an additional chemical structure or directly use the editor to draw an additional chemical structure, and then the system may automatically calculate a similarity between the chemical structures on the generated 3D-map and the additional chemical structure added by the user to generate a new 3D-map.

Figure 40:
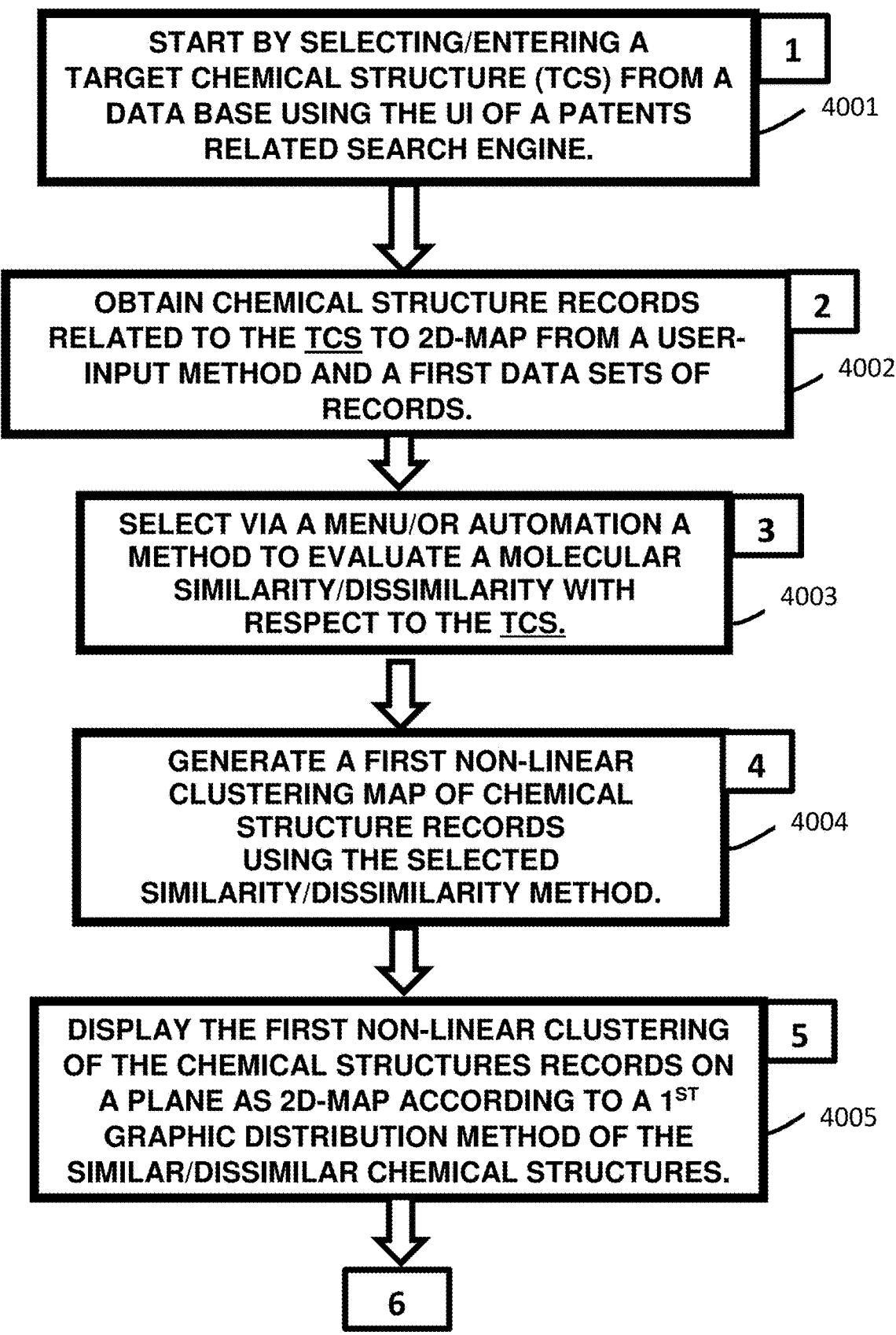
FIG. 40 is a schematic diagram of an exemplary method of practicing searches and analyses involving chemical structures utilizing an apparatus according to an embodiment of the present disclosure.
Figure 41:
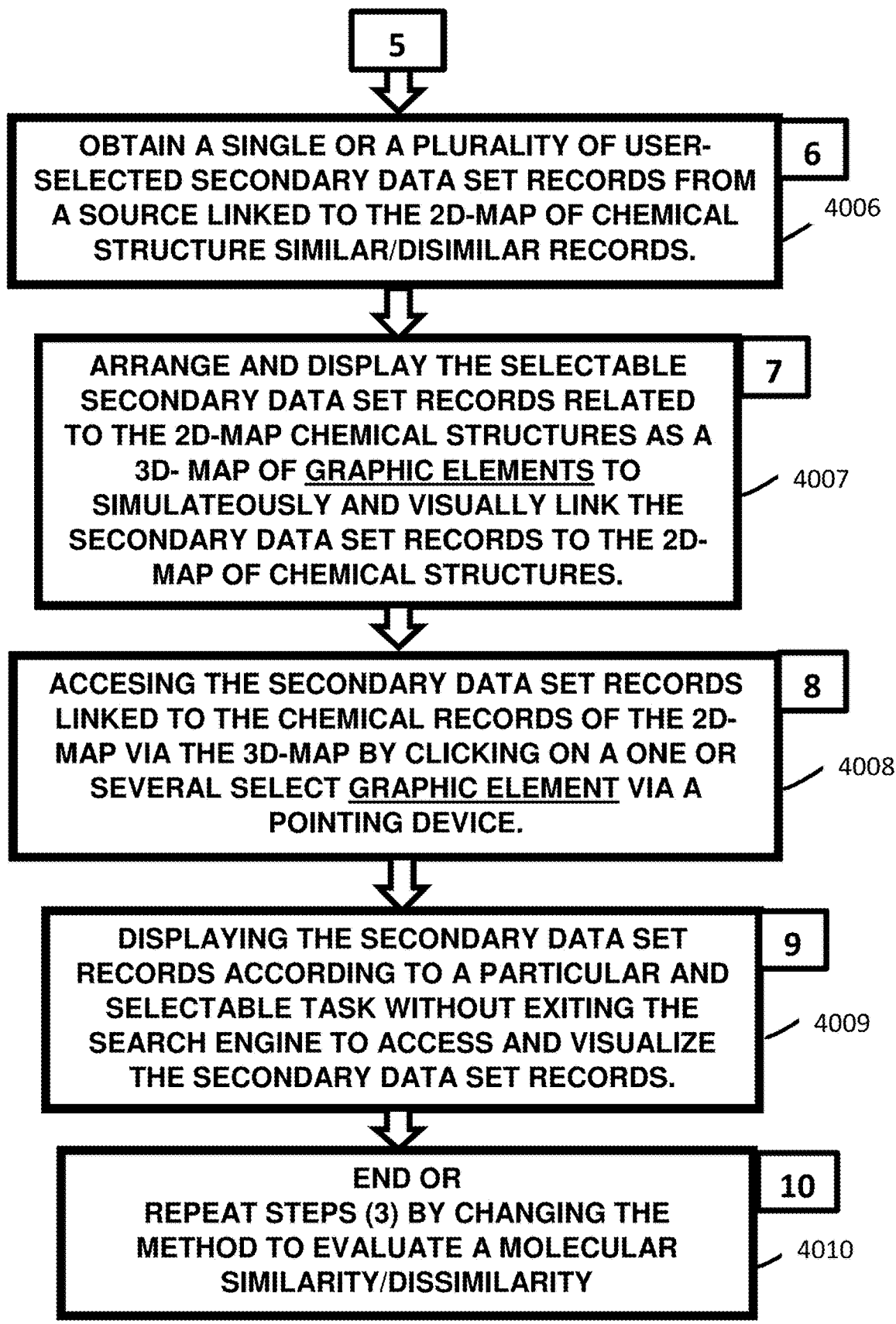
FIG. 41 is a schematic diagram of an exemplary method of practicing searches and analyses involving chemical structures utilizing an apparatus according to an embodiment of the present disclosure.

FIG. 40 is a schematic diagram of an exemplary method of practicing searches and analyses involving chemical structures utilizing an apparatus according to an embodiment of the present disclosure. FIG. 41 is a schematic diagram of an exemplary method of practicing searches and analyses involving chemical structures utilizing an apparatus according to an embodiment of the present disclosure.

Figure 42:
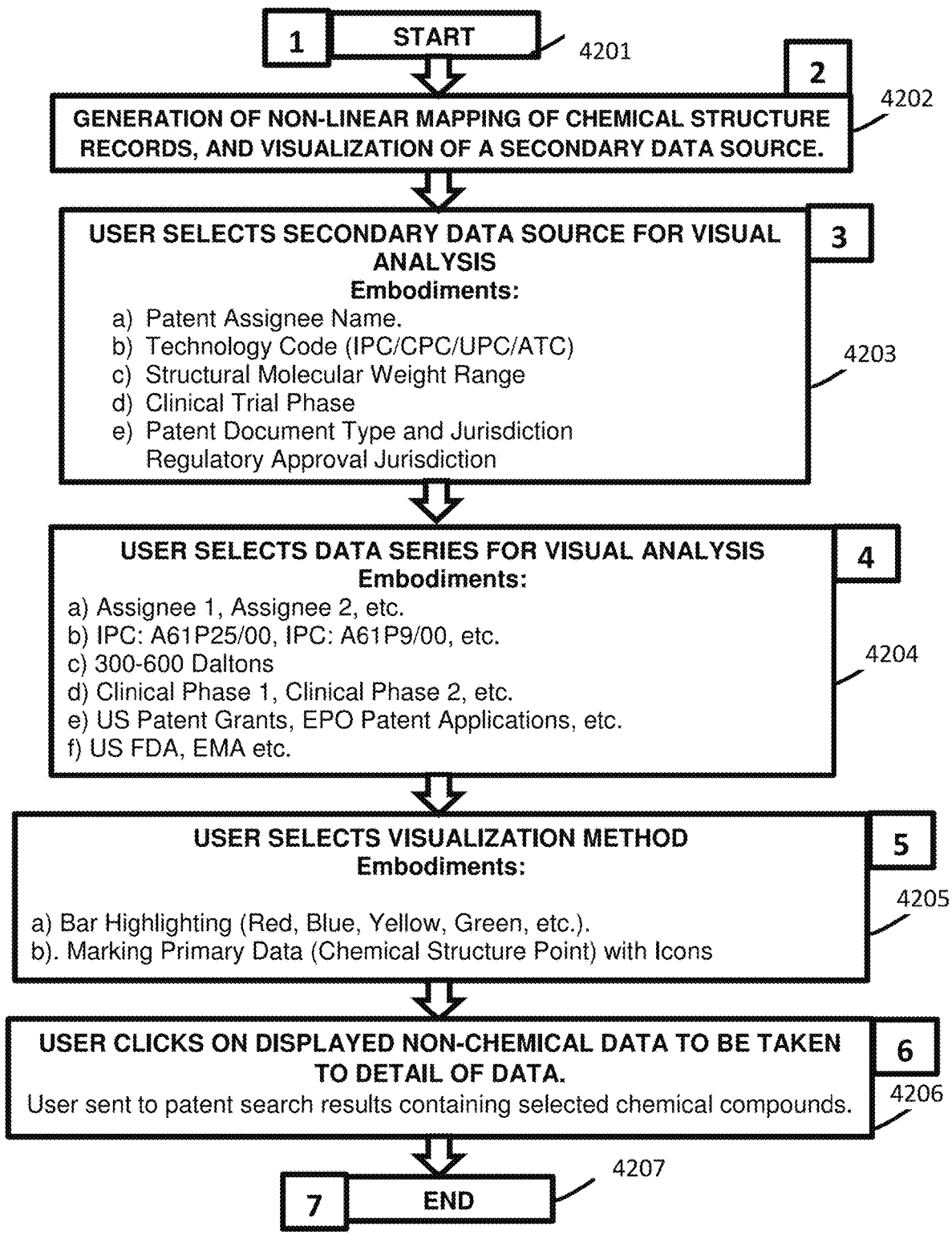
FIG. 42 is a schematic diagram of an exemplary method of practicing searches and analyses involving chemical structures and using the three-dimensional visualization tools according to an embodiment of the present disclosure.

FIG. 42 is a schematic diagram of an exemplary method of practicing searches and analyses involving chemical structures and using the three-dimensional visualization tools according to an embodiment of the present disclosure. This figure lists in detail some pieces of secondary data source information available for users to choose, such as: a patent assignee name, a technical code, a structural molecular weight range, a clinical trial phase, a patent document type, and the like.

Figure 43:
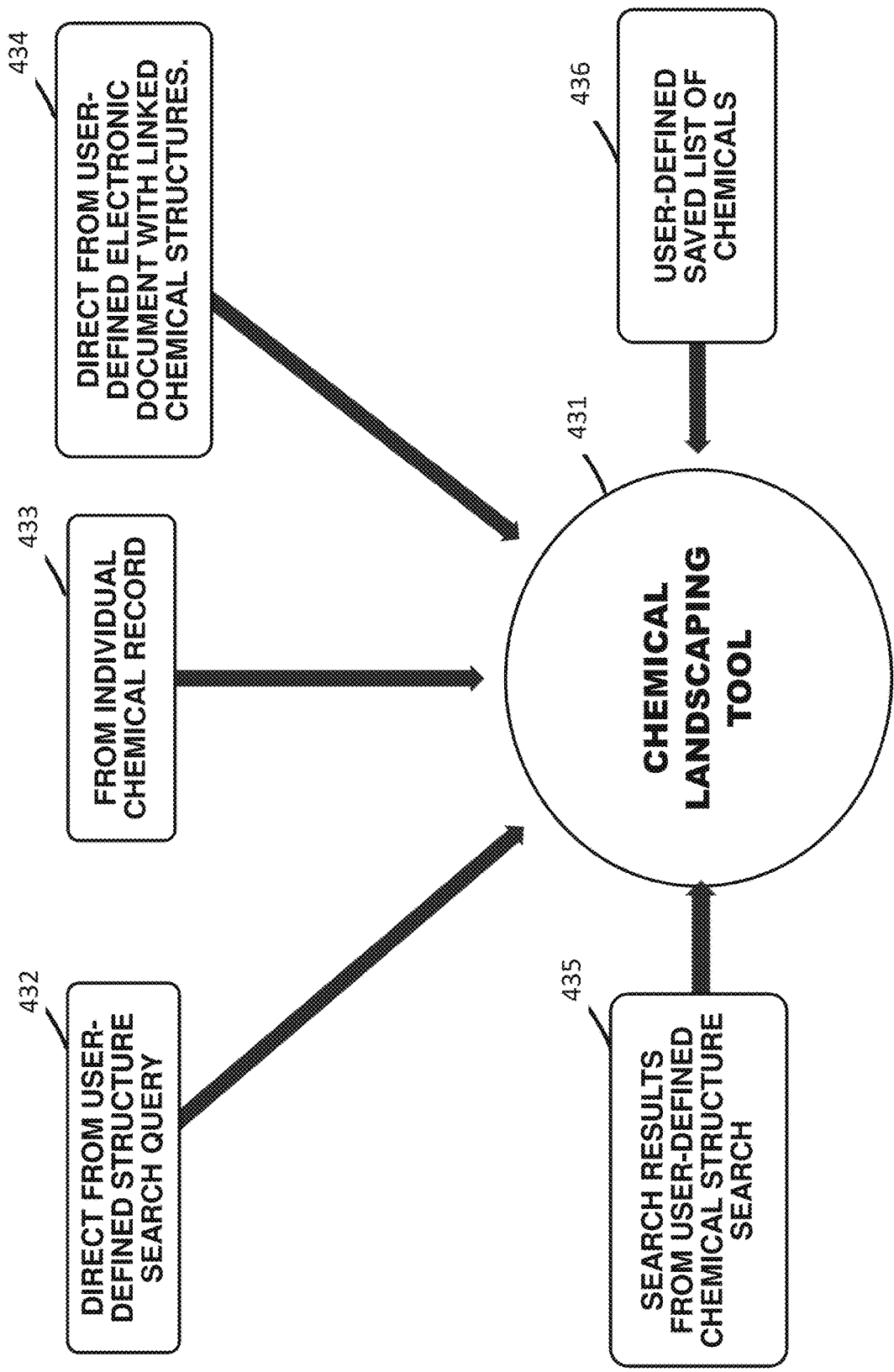
FIG. 43 is a diagram of an exemplary output as a result of practicing searches and analyses involving chemical structures using the three-dimensional visualization tools according to an embodiment of the present disclosure.

FIG. 43 is a diagram of an exemplary output as a result of practicing searches and analyses involving chemical structures using the three-dimensional visualization tools according to an embodiment of the present disclosure. In the FIG. 43, some sources of chemical structures that may be used for search and analysis are exemplified. For example, a chemical landscaping tool 431 may receive a user-defined structure search query 432, an individual chemical record 433, a user-defined electronic document with linked chemical structure 434, search results from user-defined chemical structure search 435, and a user-defined saved list of chemicals 436.

Figure 44:
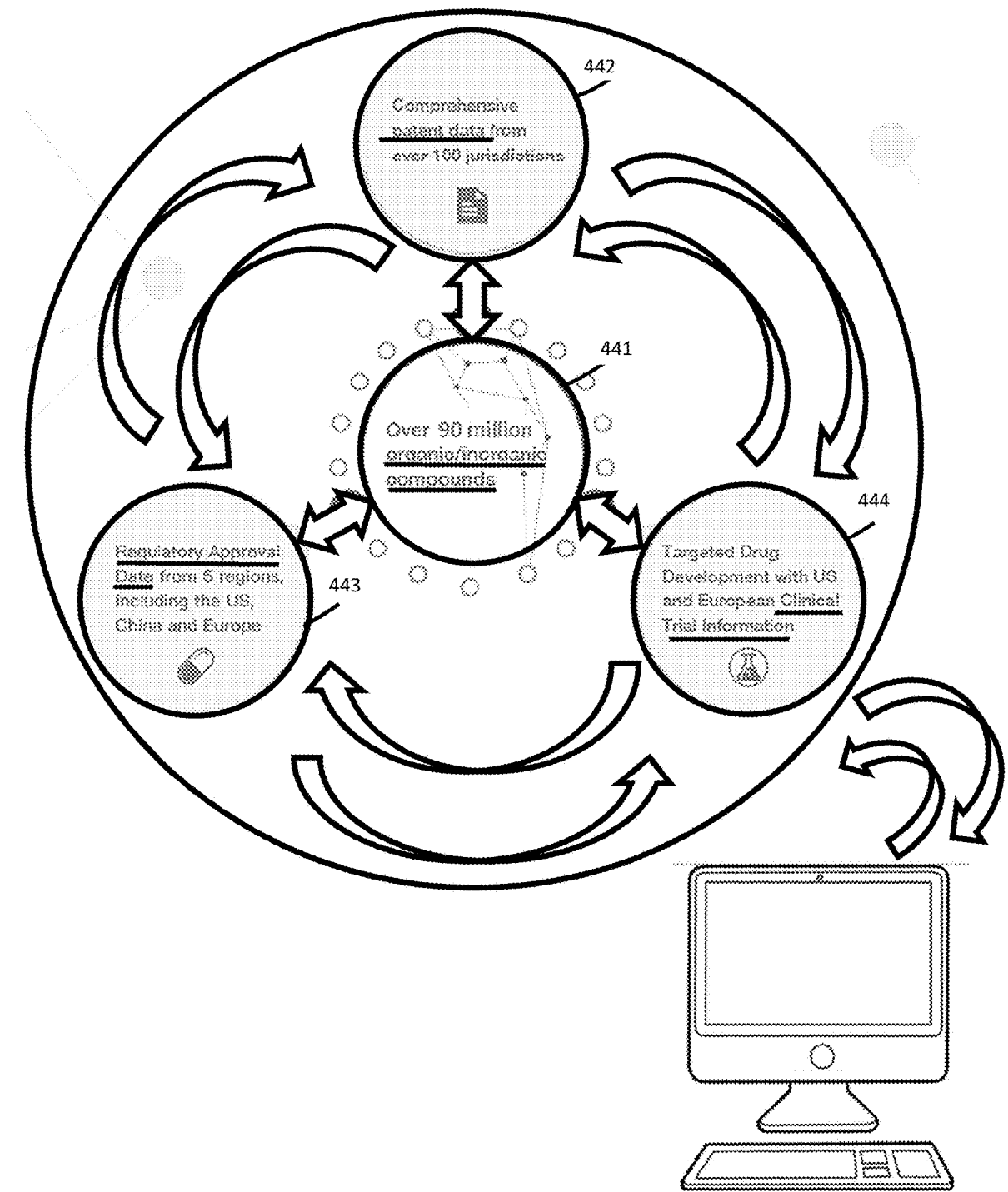
FIG. 44 is a diagram reflecting exemplary data sources and data sets searched and analyzed according to an embodiment of the present disclosure.

FIG. 44 is a diagram reflecting exemplary data sources and data sets searched and analyzed according to an embodiment of the present disclosure. The data sources of the Patsnap Chemical may include: over 90 million organic/inorganic compounds 441, comprehensive patent data 442 from over 100 jurisdictions, regulatory approval data 443 from 5 regions (including the US, China and Europe), and targeted drug development 444 with US and European clinical trial information.

Figure 45:
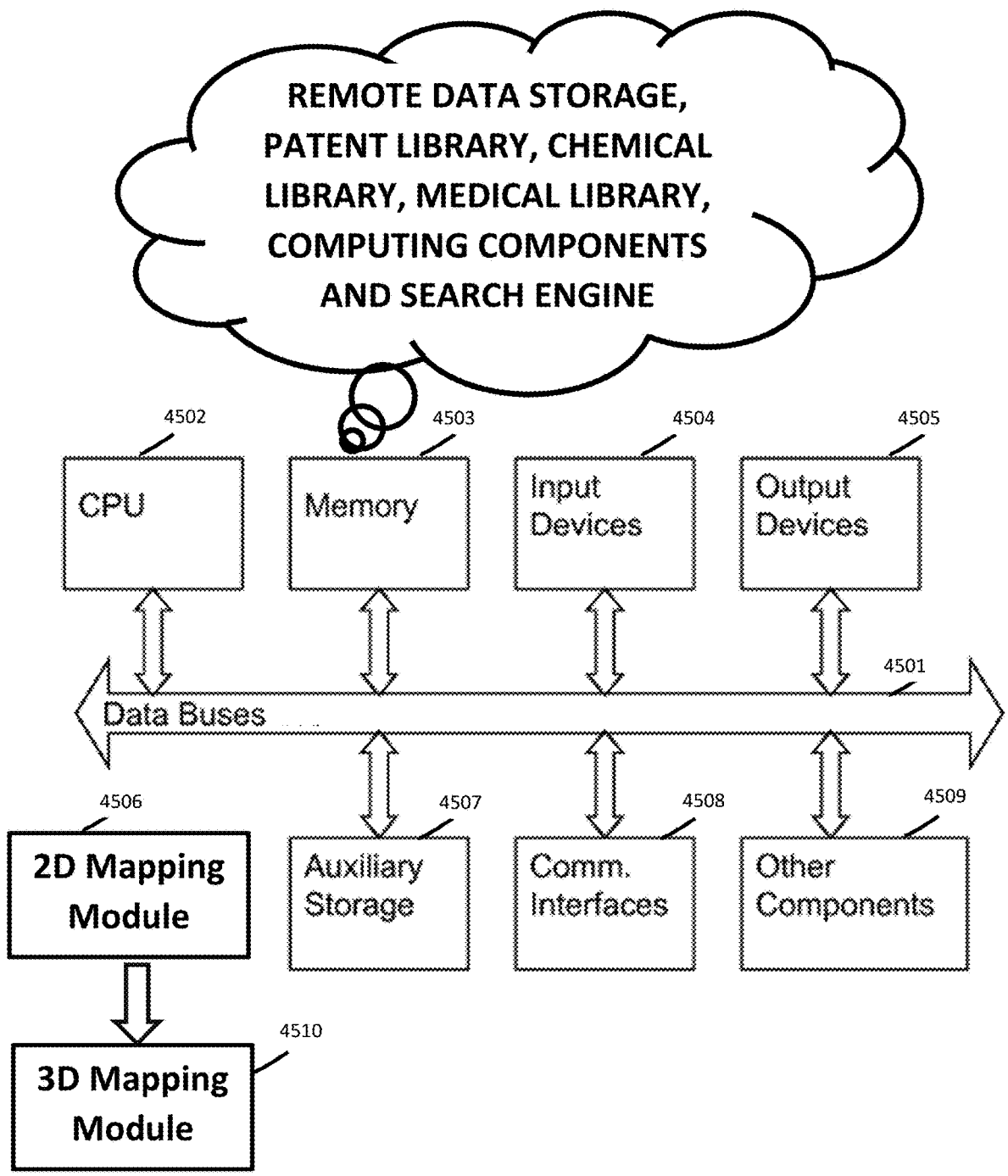
FIG. 45 is a diagram reflecting an exemplary system and set of components used to process and output the results of searches and analyses involving chemical structures using the two-dimensional or three-dimensional visualization tools according to an embodiment of the present disclosure.

FIG. 45 is a diagram reflecting an exemplary system and set of components used to process and output the results of searches and analyses involving chemical structures using the two-dimensional or three-dimensional visualization tools according to an embodiment of the present disclosure. The architecture of the Patsnap Chemical is a cloud-based service. The system may include: data buses 4501, a CPU 4502, a memory 4503, input devices 4504, output devices 4505, a 2D mapping module 4506, an auxiliary storage 4507, communication interfaces 4508, other components 4509 and a 3D mapping module 4510. Connection relationships between modules are as shown in FIG. 45.

A search apparatus is also provided. The search apparatus includes a processor and a storage device. The storage device stores processor-executable programs, and the programs include: a module configured to ask by a requesting user for literature information relating to a known chemical structure or related chemical structures; a module configured to, in response to user activities, search a collection of databases, wherein the collection of databases comprises at least one database of chemical structures and at least one database of public literature; and a module configured to identify additional literature or chemical structures that are related to or similar to the known chemical structure and associated literature thereof based on a search method.

The programs in the search apparatus further include: a module configured to select or enter the target chemical structure from the database of chemical structures using the user interface, where the user interface is associated to a patents' related search engine linked to the database of chemical structures; and a module configured to obtain from the database of chemical structures chemical structure records related to the target chemical structure to create a 2D-map or a 3D-map from a user-input method and from first data sets of chemical structure records.

The programs in the search apparatus further include: a module configured to select via a menu or automation function a first method to evaluate a molecular similarity or dissimilarity with respect to the target chemical structure, where the first method includes at least one of a Tanimoto Scoring and Fingerprinting, a Semantic similarity or a Shape similarity; a module configured to generate a first non-linear clustering map of the chemical structure records related to the target chemical structure using the selected first method; and a module configured to display the first non-linear clustering map of the chemical structure records on a plane as the 2D-map or 3D-map according to a first graphic distribution method of similar chemical structures.

The programs in the search apparatus further include: a module configured to obtain at least one of user-selected secondary data set records from one or more databases which include databases of chemical structures and databases of public literature linked to the 2D-map comprising the chemical structure records related to the target chemical structure; a module configured to arrange and display the selectable secondary data set records related to chemical structures in the 2D-map as a 3D-map of graphic elements to simultaneously and visually link the secondary data set records to the 2D-map; and a module configured to access the secondary data set records linked to the chemical structure records related to the target chemical structure of the 2D-map via the 3D-map of graphic elements by selecting at least one of graphic elements from the 3D-map of graphic elements.

The programs in the search apparatus further include: a mod a module configured to display the secondary data set records according to a selectable task without exiting the search engine to access and visualize the secondary data set records.

What is claimed is:

1. A search method, comprising: maintaining a system with at least one database of chemical structures and at least one database of public literature, wherein the public literature includes information regarding shapes of chemical structures; receiving, from a requesting user, a request for information on a shape of a target chemical structure provided by the requesting user from a user interface; and in response to the request for information on the shape of the target chemical structure, providing a set of shapes of related chemical structures to the requesting user based on the chemical similarity of the plurality of related chemical structures provided to the target chemical structure;

wherein receiving, from the requesting user, the request for information on the shape of the target chemical structure, and in response to the request for the information on the shape of the target chemical structure, providing the set of the shapes of related chemical structures to the requesting user based on the chemical similarity of the plurality of related chemical structures provided to the target chemical structure comprise:

selecting the shape of the target chemical structure from the at least one database of chemical structures or the at least one database of public literature using the user interface, wherein the user interface is associated to a patents' related search engine which is linked to the at least one database of chemical structures and the at least one database of public literature;

extracting chemical terms and convert the chemical terms into a shape of a chemical structure or extracting a shape of a chemical structure directly from a patent by utilizing a technique of semantic analysis, thereby implementing the search based on the shape of the chemical structure; and obtaining, from the at least one database of chemical structures, chemical structure records related to the shape of the target chemical structure to create a 2D-map or a 3D-map according to a user-input method and first data sets of chemical structure records, wherein the 2D-map or the 3D-map shows information of patents containing the set of the shapes of related chemical structures all of which have the chemical similarity with the target chemical structure.

2. The method according to claim 1, further comprising:
selecting via a menu or automation function a first method to evaluate a molecular similarity or dissimilarity with respect to the target chemical structure, where the first method includes at least one of a Tanimoto Scoring and Fingerprinting, a Semantic similarity or a Shape similarity;
generating a first non-linear clustering map of the chemical structure records related to the target chemical structure using the selected first method; and
displaying the first non-linear clustering map of the chemical structure records on a plane as the 2D-map or 3D-map according to a first graphic distribution method of similar chemical structures.

3. The method according to claim 2, further comprising:
obtaining at least one of user-selected secondary data set records from one or more databases which include databases of chemical structures and databases of public literature linked to the 2D-map comprising the chemical structure records related to the target chemical structure;
arranging and displaying the selectable secondary data set records related to chemical structures in the 2D-map as a 3D-map of graphic elements to simultaneously and visually link the secondary data set records to the 2D-map; and
accessing the secondary data set records linked to the chemical structure records related to the target chemical structure of the 2D-map via the 3D-map of graphic elements by selecting at least one of graphic elements from the 3D-map of graphic elements.

4. The method according to claim 3, further including the step of displaying the secondary data set records according to a selectable task without exiting the search engine to access and visualize the secondary data set records.

5. The method according to claim 2, further comprising: changing a method to evaluate a molecular similarity or dissimilarity.

6. The method according to claim 1, further comprising: arranging the chemical structures as squares across a 2D plane based on the chemical similarities in the chemical structures, wherein a similarity between adjacent chemical structures is proportional to the distance between the adjacent chemical structures.

7. The method according to claim 6, further comprising: clicking on a square reflecting grouping of similar chemical structures to display chemical structure, describe properties of the chemical structures, and provide information on and linking to a wide variety of public materials, wherein the public materials comprise scientific literature, patent materials including patent family information, medical and regulatory information.

8. The method according to claim 3, wherein the graphic elements in the 3D map are 3D columns.

9. The method according to claim 8, wherein a height of the 3D column is representative of a number of public materials mentioning the corresponding chemical structure.

10. The method according to claim 8, wherein a height of the 3D column is representative of a number of data sources involving the corresponding chemical structure.

11. The method according to claim 8, wherein a height of the 3D column is representative of a chemical entity that the corresponding chemical structure is grouped with due to the chemical similarities of chemical structures.

12. The method according to claim 1, wherein the 3D map is used to open and visualize simultaneously the chemical information and at least partially the secondary data included.

13. A search apparatus, comprising: a processor and a storage device, wherein the storage device stores processor-executable programs, and the programs comprise:
   a module configured to ask by a requesting user for literature information relating to a shape of a known chemical structure or shapes of related chemical structures;
   a module configured to, in response to user activities, search a collection of databases, wherein the collection of databases comprises at least one database of chemical structures and at least one database of public literature; and
   a module configured to identify shapes of chemical structures included in additional literature that are related to or similar to the known chemical structure and associated literature thereof based on a search method;
   wherein the module configured to, in response to user activities, search a collection of databases, and the module configured to identify the shapes of chemical structures included in the additional literature that are related to or similar to the known chemical structure and associated literature thereof based on the search method comprise:
   a module configured to select a shape of a target chemical structure from the at least one database of chemical structures or the at least one database of public literature using a user interface, wherein the user interface is associated to a patents' related search engine which is linked to the at least one database of chemical structures and the at least one database of public literature;
   a module configured to extract chemical terms and convert the chemical terms into a shape of a chemical structure or extract a shape of a chemical structure directly from a patent by utilizing a technique of semantic analysis, thereby implementing the search based on the chemical structure; and
   a module configured to obtain, from the at least one database of chemical structures, chemical structure records related to the shape of the target chemical structure to create a 2D-map or a 3D-map according to a user-input method and first data sets of chemical structure records, wherein the 2D-map or the 3D-map shows information of patents containing the set of the shapes of related chemical structures all of which have chemical similarity with the target chemical structure.

14. The search apparatus according to claim 13, wherein the programs further comprise:
   a module configured to select via a menu or automation function a first method to evaluate a molecular similarity or dissimilarity with respect to the target chemical structure, where the first method includes at least one of a Tanimoto Scoring and Fingerprinting, a Semantic similarity or a Shape similarity;
   a module configured to generate a first non-linear clustering map of the chemical structure records related to the target chemical structure using the selected first method; and
   a module configured to display the first non-linear clustering map of the chemical structure records on a plane as the 2D-map or 3D-map according to a first graphic distribution method of similar chemical structures.

15. The search apparatus according to claim 14, wherein the programs further comprise:
   a module configured to obtain at least one of user-selected secondary data set records from one or more databases which include databases of chemical structures and databases of public literature linked to the 2D-map comprising the chemical structure records related to the target chemical structure;
   a module configured to arrange and display the selectable secondary data set records related to chemical structures in the 2D-map as a 3D-map of graphic elements to simultaneously and visually link the secondary data set records to the 2D-map; and
   a module configured to access the secondary data set records linked to the chemical structure records related to the target chemical structure of the 2D-map via the 3D-map of graphic elements by selecting at least one of graphic elements from the 3D-map of graphic elements.

16. The search apparatus according to claim 15, wherein the programs further comprise: a module configured to display the secondary data set records according to a selectable task without exiting the search engine to access and visualize the secondary data set records.

17. A search system, comprising: at least one database of chemical structures, at least one database of public literature, and the search apparatus of claim 13.

* * * * *